United States Patent
Trinquet et al.

(10) Patent No.: US 8,697,372 B2
(45) Date of Patent: Apr. 15, 2014

(54) METHOD FOR DETERMINING THE BINDING OF A GIVEN COMPOUND TO A MEMBRANE RECEPTOR

(75) Inventors: Eric Trinquet, Pont-Saint-Esprit (FR); Jurriaan Zwier, Rochefort du Gard (FR); Gérard Mathis, Bagnols sur Ceze (FR); Jean-Philippe Pin, Montpellier (FR); Thierry Durroux, Saint Gely-du-Fesc (FR)

(73) Assignees: CIS Bio International, Gif sure Yvette Cedex (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/388,150

(22) PCT Filed: Aug. 12, 2010

(86) PCT No.: PCT/FR2010/051700
§ 371 (c)(1),
(2), (4) Date: Apr. 2, 2012

(87) PCT Pub. No.: WO2011/018586
PCT Pub. Date: Feb. 17, 2011

(65) Prior Publication Data
US 2012/0190048 A1    Jul. 26, 2012

(30) Foreign Application Priority Data
Aug. 13, 2009  (FR) .................................... 09 55667

(51) Int. Cl.
*G01N 33/566* (2006.01)
*C07K 19/00* (2006.01)
*C07K 14/705* (2006.01)

(52) U.S. Cl.
USPC .......................... 435/7.21; 435/69.7; 436/501

(58) Field of Classification Search
None
See application file for complete search history.

(56) References Cited

U.S. PATENT DOCUMENTS

| | | | |
|---|---|---|---|
| 4,637,988 A | 1/1987 | Hinshaw et al. | |
| 4,670,572 A | 6/1987 | Hinshaw et al. | |
| 4,761,481 A | 8/1988 | Hale et al. | |
| 4,767,718 A | 8/1988 | Meyers | |
| 4,794,191 A | 12/1988 | Hinshaw et al. | |
| 4,801,722 A | 1/1989 | Hinshaw et al. | |
| 4,837,169 A | 6/1989 | Toner | |
| 4,859,777 A | 8/1989 | Toner | |
| 4,927,923 A | 5/1990 | Mathis et al. | |
| 5,032,677 A | 7/1991 | Hale et al. | |
| 5,055,578 A | 10/1991 | Hale et al. | |
| 5,106,957 A | 4/1992 | Hale et al. | |
| 5,116,989 A | 5/1992 | Hale et al. | |
| 5,202,423 A | 4/1993 | Kankare et al. | |
| 5,234,825 A | 8/1993 | McCleary | |
| 5,316,909 A | 5/1994 | Xu | |
| 5,457,184 A | 10/1995 | Lehn et al. | |
| 5,622,821 A | 4/1997 | Selvin et al. | |
| 2008/0014599 A1 | 1/2008 | Wechsler et al. | |
| 2009/0162861 A1 | 6/2009 | Mathis et al. | |
| 2009/0220988 A1 | 9/2009 | Trinquet et al. | |

FOREIGN PATENT DOCUMENTS

| | | |
|---|---|---|
| EP | 0180492 | 5/1986 |
| EP | 0321353 | 6/1989 |
| EP | 0403593 | 12/1990 |
| EP | 0601113 | 6/1994 |
| FR | 2 890 174 A1 | 3/2007 |
| WO | WO 90/00550 | 1/1990 |
| WO | WO 93/05049 | 3/1993 |
| WO | WO 00/12544 | 3/2000 |
| WO | WO 01/96877 | 12/2001 |
| WO | WO 2004/072232 | 8/2004 |
| WO | WO 2004/088312 | 10/2004 |
| WO | WO2007/116069 | 10/2007 |
| WO | WO2008/001361 | 1/2008 |
| WO | WO 2008/063721 | 5/2008 |
| WO | WO 2009/010580 | 1/2009 |

OTHER PUBLICATIONS

Monnier et al., Trans-activation between 7TM domains: implication in heterodimeric GABAB receptor activation, Jun. 5, 2011, The EMBO Journal 30(1): 32-42.*

Liu et al., Molecular Determinants Involved in the Allosteric Control of Agonist Affinity in the GABAB Receptor by the GABAB2 Subunit, Apr. 16, 2004, The Journal of Biological Chemistry 279(16):15824-15830.*

Maurel D. et al., "Cell Surface Detection of Membrane Protein Interaction With Homogenous Time-Resolved Fluorescence Resonance Energy Transfer Technology", Analytical Biochemistry, Academic Press Inc, New York, vol. 329, No. 2, Jun. 15, 2004, ( pp. 253-262), XP004509821, ISSN: 0003-2697.

Maurel D. et al., "Cell-Surface Protein-Protein Interaction Analysis With Time-Resolved FRET and Snap-Tag Technologies: Application to GPCR Oligomerization", Nature Methods, Nature Publishing Group, GB, vol. 5, No. 6, Jun. 1, 2008, (pp. 561-567) X002556321, ISSN: 1548-7091.

Millgan, "Applications of Bioluminescence- And Fluorescence Resonance Energy Transfer to Drug Discovery At G Protein-Coupled Receptors", European Journal of Pharmaceutical Sciences, Elsevier, Amsterdam, NL, vol. 21, No. 4, Mar. 1, 2004 (pp. 397-405). XP002350686, ISSN: 0928-0987.

Ilien B et al., "Fluorescence Resonance Energy Transfer to Probe Human M1 Muscarinic Receptor Structure and Drug Binding Properties", Journel of Neurochemistry Wiley Interscience, New York, NY, US, vol. 85, No. 3, May 1, 2003, (pp. 768-778), XP002265260, ISSN: 0022-3042.

(Continued)

*Primary Examiner* — John Ulm
(74) *Attorney, Agent, or Firm* — Hamre, Schumann, Mueller & Larson, P.C.

(57) ABSTRACT

The invention relates to a method for determining whether a test compound binds preferentially to a membrane receptor R1 or to a membrane receptor R2, these receptors being known to be expressed on the surface of the cells in monomeric, homodimeric or heterodimeric form. This method is applied using one or two FRET partner pairs.

20 Claims, 11 Drawing Sheets

(56) References Cited

OTHER PUBLICATIONS

George et al.: "G-Protein-Coupled Receptor Oligomerization and Its Potential for Drug Discovery"; Nature Drug Discovery 1, Oct. 2002, pp. 808-820.

Milligan: "G protein-coupled receptor dimerisation: Molecular basis and relevance to function"; Biochimica et Biophysica Acta 1768 (2007), pp. 825-835.

Pramanik et al.: "Fluorescence Correlation Spectroscopy Detects Galanin Receptor Diversity on Insulinoma Cells"; Biochemistry 2001, 40, pp. 10839-10845.

Handl et al.: "Lanthanide-based time-resolved fluorescence of in cyto ligand-receptor interactions"; Analytical Biochemistry 330 (2004), pp. 242-250.

Gagne et al.: "Use of Fluorescence Polarization Detection for the Measurement of Fluopeptide™ Binding to G Protein-Coupled Receptors"; Journal of Receptors and Signal Transduction, vol. 22, Nos. 1-4, pp. 333-343, 2002.

Poole et al.: "Synthesis and characterisation of highly emissive and kinetically stable lanthanide complexes suitable for usage 'in cellulo'"; The Royal Society of Chemistry 2005, Org. Biomol. Chem., 2005, 3, pp. 1013-1024.

Griffin et al.: "Specific Covalent Labeling of Recombinant Protein Molecules Inside Live Cells"; Science 281, pp. 269-271 (1998).

Adams et al.: "New Biarsenical Ligands and Tetracysteine Motifs for Protein Labeling in Vitro and in Vivo: Synthesis and Biological Applications"; JACS Articles, J. Am. Chem. Soc. 2002, 124, pp. 6063-6076.

McCann et al.: "Peptide tags for labeling membrane proteins in live cells with multiple fluorophores"; BioTechniques vol. 38, No. 6, pp. 945-952 (Jun. 2005).

Juillerat et al.: "Directed Evolution of $O^6$-Alkylguanine-DNA Alkyltransferase for Efficient Labeling of Fusion Proteins with Small Molecules In Vivo", Chemistry & Biology, vol. 10, pp. 313-317, Apr. 2003.

Gautier et al.: "An Engineered Protein Tag for Multiprotein Labeling in Living Cells"; Chemistry & Biology, vol. 15, pp. 128-136, Feb. 2008.

Gronemeyer et al.: "Directed evolution of $O^6$-alkylguanine-DNA alkyltransferace for applications in protein labeling"; Protein Engineering, Design & Selection, vol. 19, No. 7, pp. 309-316, 2006.

George et al.: "Specific Labeling of Cell Surface Proteins with Chemically Diverse Compounds"; JACS Communications, J. Am. Chem. Soc. 2004, 126, pp. 8896-8897.

Maurel et al.: "Cell-surface protein-protein interaction analysis with time-resolved FRET and snap-tag technologies: application to GPCR oligomerization"; Nature Methods, 2008, Supplementary methods.

Okuno et al.: "GLIDA: GPCR—ligand database for chemical genomics drug discovery—database and tools update"; Nucleic Acids Research, 2008, vol. 36, Database issue D907-D912.

Kricka: "Nonisotopic Probing, Blotting, and Sequencing"; Second Edition, Academic Press, pp. 66-72, 1995.

Middleton et al.: "Fluorophore-tagged GPCR ligands"; Current Opinion in Chemical Biology 2005, 9, pp. 517-525.

Beaudet et al.: "Fluorescent ligands for studying neuropeptide receptors by confocal microscopy"; Brazilian Journal of Medical and Biological Research (1998) 31(11), pp. 1479-1489.

Durroux et al.: "Fluorescent Pseudo-Peptide Linear Vasopressin Antagonists: Design, Synthesis, and Applications"; Journal of Medicinal Chemistry, Apr. 1999, 42, pp. 1312-1319.

Hein et al.: "Intracellular Trafficking of Angiotensin II and its $AT_1$ and $AT_2$ Receptors: Evidence for Selective Sorting of Receptor and Ligand"; Molecular Endocrinology, Aug. 1997, 11(9), pp. 1266-1277.

Bakthavachalam et al.: "Fluorescent Probes for Dopamine Receptors: Synthesis and Characterization of Fluorescein and 7-Nitrobenz-2-oxa-1,3-diazol-4-yl Conjugates of D-1 and D-2 Receptor Ligands"; Journal of Medicinal Chemistry, 1991, 34(11), pp. 3235-3241.

Manning et al.: "Potent $V_2/V_{1a}$ Vasopressin Antagonists with C-Terminal Ethylenediamine-Linked Retro-Amino Acids"; Journal of Medicinal Chemistry, Oct. 1992, 35(12), pp. 3895-3904.

Harmar et al.: "IUPHAR-DB: the IUPHAR database of G protein-coupled receptors and ion channels"; Nucleic Acids Research, 2009, vol. 37, Database issue, D680-D685.

\* cited by examiner

| Proteins in the cell membrane: monomers and homodimers | | | | |
|---|---|---|---|---|
| Without test compound | Signal $L_1$ | Signal $L_1$ | Signal $L_2$ | Signal $L_2$ |
| + compound binding to $R_1$ and $R_1R_1$ | Signal $L_1$ suppressed | | Signal $L_2$ | Signal $L_2$ |
| + compound binding to $R_2$ and $R_2R_2$ | Signal $L_1$ | Signal $L_1$ | | Signal $L_2$ suppressed |
| + compound binding simultaneously to $R_1$, $R_1R_1$, $R_2$ and $R_2R_2$ | Signals $L_1$ and $L_2$ suppressed | | | |

FIG. 1

| Proteins in the cell membrane: monomers, homodimers and heterodimers | (monomer R₁) | (heterodimer R₁R₂) | (monomer R₂) | (homodimer R₂R₂) | (heterodimer with both) |
|---|---|---|---|---|---|
| without test compound | Signal L₂ | Signal L₂ | No signal | No signal | Signal L₁ + Signal L₂ |
| + compound binding to R₂, R₂R₂, but not to R₁R₂ | Signal L₂ suppressed | | No signal | No signal | Signal L₁ + Signal L₂ |
| + compound binding only to R₁R₂ | Signal L₂ | Signal L₂ suppressed | No signal | No signal | Signal L₁ and L₂ suppressed |
| + compound binding simultaneously to R₂, R₂R₂ and | Signal L₂ suppressed | Signal L₂ suppressed | No signal | No signal | Signal L₁ and L₂ suppressed |

FIG. 4

METHOD FOR DETERMINING THE BINDING OF A GIVEN COMPOUND TO A MEMBRANE RECEPTOR

PRIOR ART

The invention relates to the area of screening of compounds capable of binding to membrane receptors.

The binding of extracellular ligands to their membrane receptors constitutes the first step in the transduction of biochemical signals from the exterior to the interior of living cells and is therefore an essential element in the regulation of these cells. The membrane receptors therefore constitute a target of choice for screening new molecules capable of regulating biological processes, in particular for screening new medicinal products.

It has been established that membrane receptors can function not only alone, but also in the form of homodimers or heterodimers (S. R. George et al., Nature drug discovery 1, 808-820 (2002) and G. Milligan, Biochimica et Biophysica Acta 1768, 825-835). Certain membrane receptors are only functional in the form of dimer, this is the case for example for the receptor of gamma-aminobutyric acid (GABAB), which consists of a subunit GABAB1 and GABAB2. The majority of metabotropic glutamate receptors function in the form of homodimers.

There are numerous methods for determining whether a given compound does or does not bind to a membrane receptor. The most classical method consists of labeling the test compound with a radioactive atom (tritium, iodine 125), putting it in contact with the cells expressing the receptor of interest, and counting the radioactivity fixed to the cell after washing. It is also common to label a known ligand of a receptor, and measure the capacity of a test compound to compete with this labeled ligand for the binding site to the receptor. These methods have several drawbacks: they are based on the use of radioactive compounds, which poses problems of safety and waste treatment, and they can be difficult to employ on high-throughput platforms, i.e. when rapid testing of thousands of compounds is required. They also do not allow information to be obtained regarding the receptor to which the test compounds bind, in particular it is impossible to determine whether the test compound binds to one type of receptor or to several, to a monomeric receptor or to a dimeric receptor.

Other methods have been described, notably methods based on the use of fluorescent compounds.

Fluorescence correlation spectroscopy ("FCS") makes it possible for example to measure the fluctuations of fluorescence of molecules diffusing in a medium exposed to a confocal laser. As the time of diffusion of these molecules is dependent on the coefficient of diffusion, which is itself correlated with the size of said molecules, the data collected by FCS can be used for differentiating molecules with rapid diffusion from those with slow diffusion, and consequently the ligands bound to their receptor from those that are not. This technique has been applied for example to investigation of galanin receptors, using galanin labeled with rhodamine (Pramanik, A. et al., 2001. Fluorescence correlation spectroscopy detects galanin receptor diversity on insulinoma cells. *Biochemistry*, 40(36), 10839-10845).

Handl, H. L. et al. (2004. Lanthanide-based time-resolved fluorescence of in cyto ligand-receptor interactions, *Analytical Biochemistry*, 330(2), 242-250) described an alternative to investigations of binding by competition with radioactive ligands, based on the DELFIA (Diffusion enhanced lanthanide fluoroimmunoassay) technique. According to this technique, a ligand labeled with a weakly fluorescent lanthanide chelate is put in contact with a cell expressing the receptors under investigation. After a washing step that is intended to remove the unbound ligand, a solution intended to amplify the fluorescence of the lanthanide is added to the measuring medium. This approach was used by the authors in experiments of binding of a derivative of α-MSH conjugated to a chelate of europium, with the melanocortin receptor MC4.

Fluorescence polarization (FP) is another technique that has been used as an alternative to the use of radiolabeled ligands: Gagne, A et al. for example described the preparation of ligands of G protein-coupled receptors (GPCR) labeled with a fluorophore known by the trade name Bodypy™. In particular, ligands of the receptors of melanin concentrating hormone, of bradykinin and of melanocortin were labeled with this fluorophore and their binding to these receptors was investigated by measuring the variations in polarization of the fluorescence emitted by the measuring medium (2002. Use of fluorescence polarization detection for the measurement of fluopeptide binding to G protein-coupled receptors, *Journal of Receptor and Signal Transduction Research*, 22(1-4), 333-343).

The invention proposes to provide a novel method of screening of compounds capable of binding to membrane receptors, in particular for determining whether a compound binds preferentially to dimers of receptors, notably heterodimers of GPCR.

SUMMARY OF THE INVENTION

The invention relates to a method for determining whether a test compound binds preferentially to a membrane receptor R1 or to a membrane receptor R2, these receptors being known to be expressed on the surface of the cells in monomeric or homodimeric form, i.e. they are present on the surface of the cells in the form of monomers R1 or R2, or in the form of homodimers R1R1 or R2R2. This method also makes it possible to determine whether a test compound binds indiscriminately to these receptors regardless of their state of dimerization.

This method can also be employed with receptors forming oligomers, in particular with receptors forming trimers, tetramers or pentamers.

The method according to the invention also makes it possible to determine whether a test compound binds to heterodimers R1R2, R1 and R2 representing receptors known to be expressed on the surface of the cells in monomeric, homodimeric or heterodimeric form, i.e. they are present on the surface of the cells in the form of monomers R1 or R2, in the form of homodimers R1R1 or R2R2, or in the form of heterodimers R1R2.

In this aspect of the invention, it is possible not only to determine whether the test compound binds to heterodimers R1R2, but also to establish whether the test compound also binds to monomers R2 and to homodimers R2R2, or whether it binds specifically to monomers R2 or to homodimers R2R2 and not to heterodimers R1R2.

The method according to the invention is based on the use of FRET partner pairs, one of the members of which is conjugated to a ligand of one or of both receptors under investigation, and the other is conjugated to one of the receptors under investigation. This method employs one or two FRET partner pairs.

BRIEF DESCRIPTION OF THE DRAWINGS

FIGS. 1 and 2 represent an aspect of the invention where the receptors R1 and R2 are expressed on the surface of the cells in monomeric or homodimeric form.

FIGS. 3 and 4 represent an aspect of the invention where the receptors R1 and R2 are expressed on the surface of the cells in monomeric, homodimeric or heterodimeric form.

DETAILED DESCRIPTION

According to a first aspect, the method of the invention is applied on membrane receptors R1 and R2 expressed in the cell membranes, these receptors being known to be present in monomeric, homodimeric, but not heterodimeric form, and makes it possible to determine whether a test compound binds preferentially to one or other of these receptors regardless of their state of dimerization, or to determine whether this compound binds indiscriminately to these receptors regardless of their state of dimerization.

According to one embodiment of this first aspect (shown in FIG. 1), the method according to the invention is a method for determining the binding of a test compound with receptors R1 and R2 expressed in the cell membranes, these receptors being known to be present in homodimeric but not heterodimeric form, said method comprising the following steps:

(a) Labeling of the receptor R1 covalently or noncovalently with a first energy donor compound D1 and of the receptor R2 covalently or noncovalently with a second energy donor compound D2, (b) Addition, to the measuring medium, of a ligand known to be capable of binding to the receptors R1, R2 and to the homodimers R1R1 and R2R2, said ligand being labeled with an energy acceptor compound A, and the pairs (D1,A) and (D2,A) each forming FRET partner pairs, (c) Measurement of the total luminescence $L_{tot}$ emitted at the emission wavelength of the acceptor compound A, (d) Addition of a compound extinguishing the FRET signal of the pair (D1,A), (e) Measurement of the luminescence $L_2$ emitted at the emission wavelength of the acceptor compound A, (f) Determination of the luminescence $L_1$ due to the pair (D1,A) from the formula $$L_1 = L_{tot} - L_2$$

the sequence of steps (c) to (f) being applied in the presence and in the absence of the test compound.

According to this embodiment:

disappearance of the luminescence L1 and maintenance of the luminescence L2 in the presence of the test compound are representative of the binding of the test compound to the receptor R1 and to the homodimer R1R1, disappearance of the luminescence L2 and maintenance of the luminescence L1 in the presence of the test compound are representative of the binding of the test compound to the receptor R2 and to the homodimer R2R2, disappearance of the luminescence L1 and disappearance of the luminescence L2 in the presence of the test compound are representative of a compound binding both to the receptors R1, R2, and to the homodimers R1R1 or R2R2, The FRET extinguishing compounds required for application of this method are described in international patent application WO 2007/116069. Preferably, the donor compound D1 is a lanthanide complex, in particular a lanthanide cryptate or chelate (such as a cryptate or a chelate of terbium or of europium) and the FRET extinguishing compound of the pair (D1,A) is a compound having a binding domain with D1, in particular a specific antibody of the lanthanide complex D1.

Figure 2:
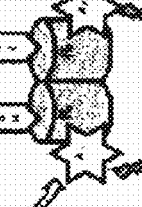

According to another embodiment of the first aspect (shown in FIG. 2), the method according to the invention can be applied by labeling the receptors R1 and R2 with FRET acceptor compounds A1 and A2 and the ligand with a donor D1, which corresponds to the format opposite to that presented in the preceding embodiment. Thus, according to this embodiment, the two FRET partner pairs used are (D,A1) and (D,A2).

This second embodiment therefore relates to a method for determining the binding of a test compound with membrane receptors R1 and R2 expressed in the cell membranes, these receptors being known to be present in homodimeric but not heterodimeric form, said method comprising the following steps:

(a) Labeling of the receptor R1 covalently or noncovalently with a first energy acceptor compound $A_1$ and of the receptor R2 covalently or noncovalently with a second energy acceptor compound A2, A1 and A2 having different emission wavelengths, (b) Addition, to the measuring medium, of a ligand known to be capable of binding to the receptors R1, R2 and to the homodimers R1R1 and R2R2, this ligand being labeled with an energy donor compound D, and the pairs (D,A1) and (D,A2) each forming FRET partner pairs, (c) Measurement of the luminescence $L_1$ emitted at the emission wavelength of the acceptor compound A1 on the one hand, and of the luminescence $L_2$ emitted at the emission wavelength of the acceptor compound A2 on the other hand, each in the presence and in the absence of the test compound.

According to this second embodiment:

disappearance of the luminescence L1 and maintenance of the luminescence L2 in the presence of the test compound are representative of the binding of the test compound to the receptor R1 and to the homodimer R1R1, disappearance of the luminescence L2 and maintenance of the luminescence L1 in the presence of the test compound are representative of the binding of the test compound to the receptor R2 and to the homodimer R2R2, disappearance of the luminescence L1 and disappearance of the luminescence L2 in the presence of the test compound are representative of a compound binding both to the receptors R1, R2, and to the homodimers R1R1 or R2R2.

According to a second aspect, the method of the invention is applied on membrane receptors R1 and R2 expressed in the cell membranes, these receptors being known to be present in heterodimeric, and optionally monomeric and/or homodimeric form, and makes it possible to determine (i) whether a test compound binds to the heterodimers R1R2, and (ii) whether a test compound binds specifically to the heterodimers R1R2, or else whether it binds specifically to the receptor R2 and to the homodimer R2R2, or whether it binds both to the receptor R2, to the homodimer R2R2 and to the heterodimer R1R2.

Figure 3:
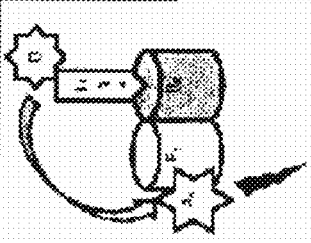
Figure 5:
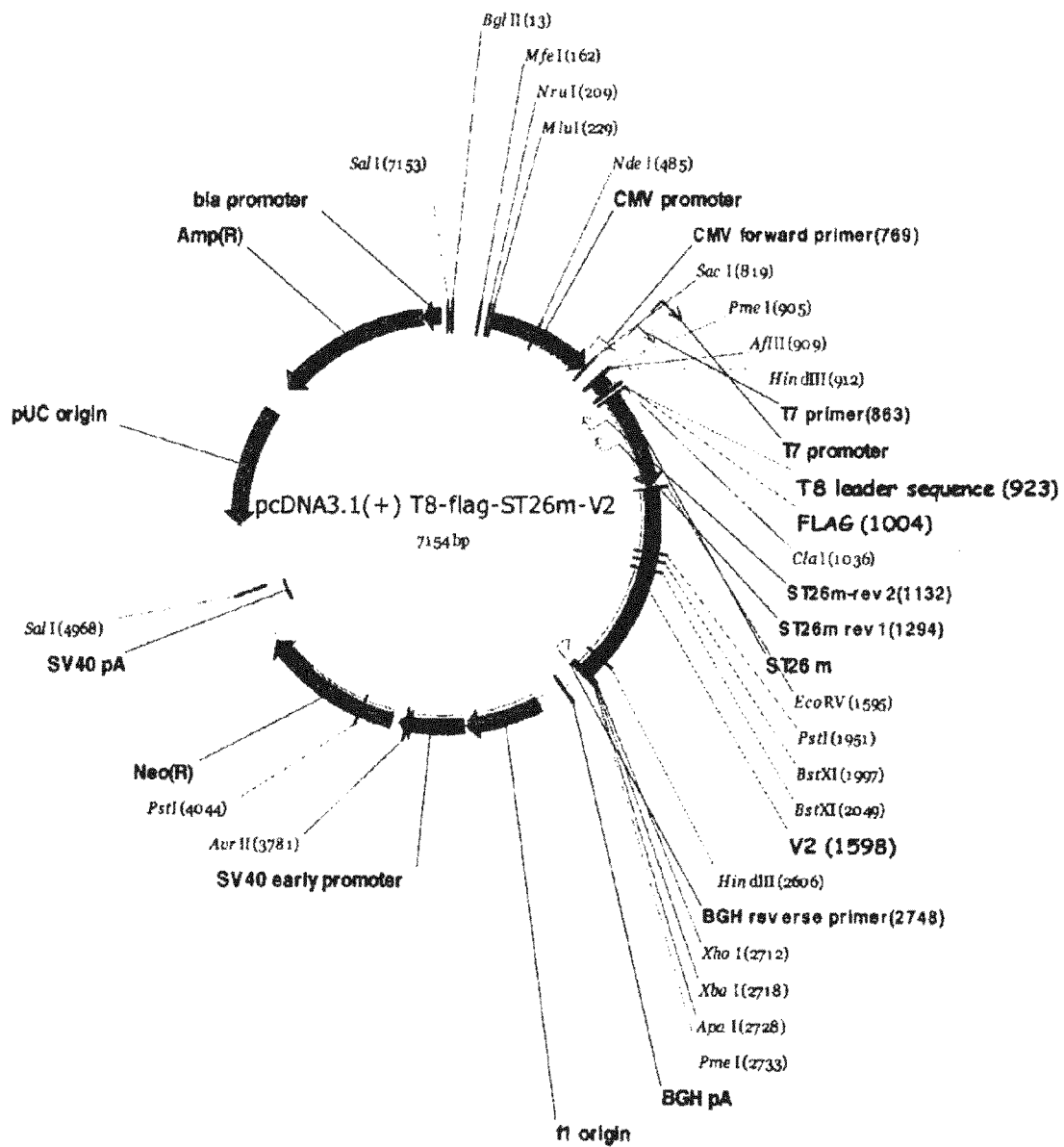
FIG. 5 represents the FLAG-ST-V2R plasmid.
Figure 6:
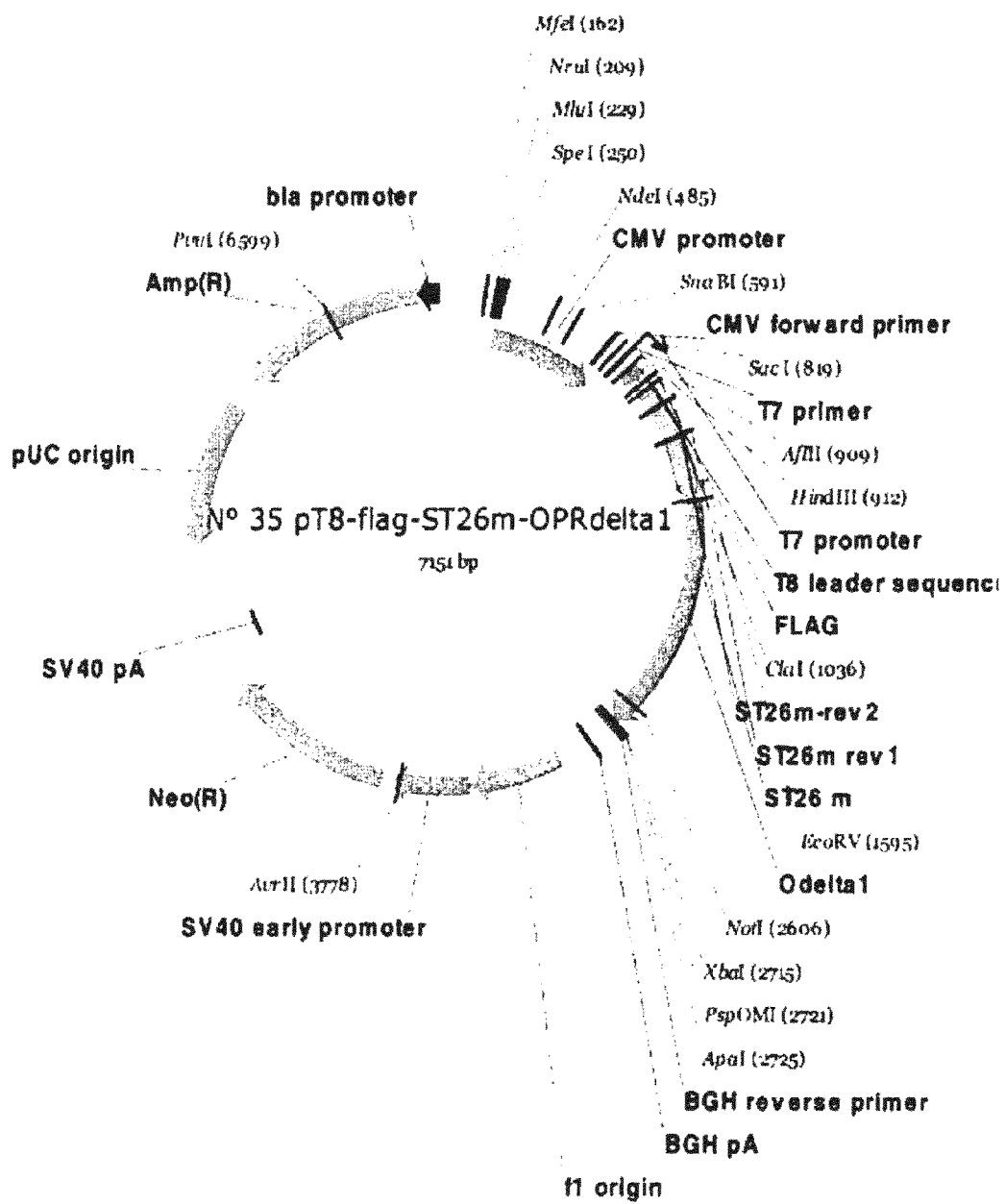
FIG. 6 represents the FLAG-SNAP-delta Opioid plasmid.
Figure 7:
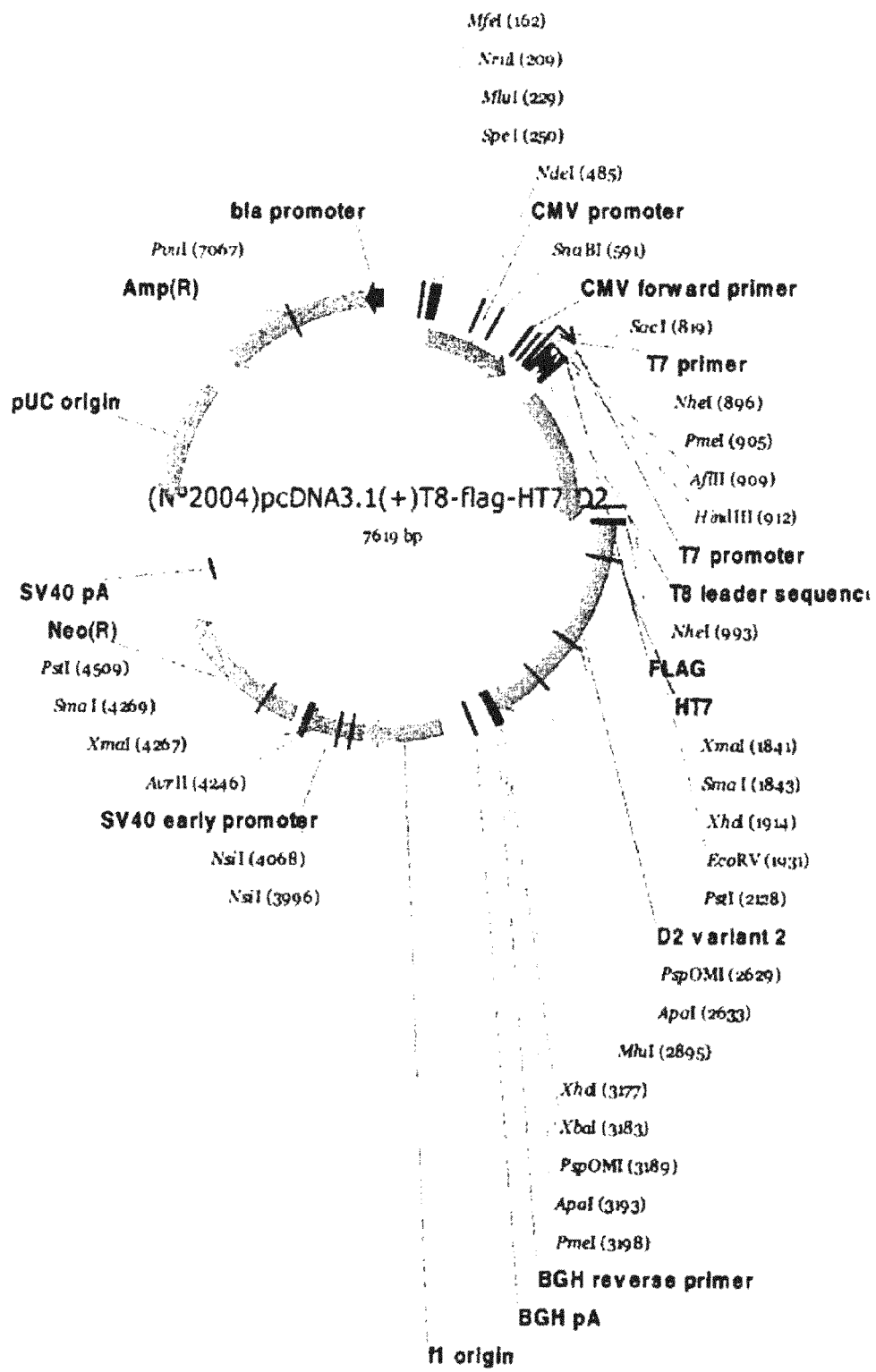
FIG. 7 represents the FLAG-Halo-Dopamine D2 plasmid.

According to one embodiment of this second aspect (shown in FIG. 3), the method according to the invention is a method for determining the binding of a test compound with membrane receptors R1 and R2 expressed in the cell membranes, these receptors being known to be present in heterodimeric form (optionally also in monomeric or homodimeric form), said method comprising the following steps:

(a) Labeling of the receptor R1 covalently or noncovalently with the first member of a FRET partner pair (D,A1), in which D is the energy donor compound and A1 is the energy acceptor compound, (b) Addition, to the measuring medium, of a known ligand of R2 capable of binding to the heterodimer R1R2 but neither to the receptor R1 nor to the homodimer R1R1, said ligand being labeled with the second member of said FRET partner pair, (c) Measurement of the luminescence $L_1$ emitted at the emission wavelength of the acceptor compound A1, in the presence and in the absence of the test compound.

According to this embodiment, disappearance of the luminescence L1 in the presence of the test compound is representative of the binding of this compound to the heterodimer R1R2.

The first member of the FRET partner pair, which labels the receptor R1, can be an energy donor compound D and the second member, which is bound to the ligand, can be an acceptor compound A1. The reversed format can also be used, namely, the first member of the FRET partner pair, which labels R1, can be an energy acceptor compound A1 and the second member of this pair, bound to the ligand, can be an energy donor compound D.

According to other embodiment of the second aspect (shown in FIG. 4), the ligand is conjugated with a donor compound D, the receptor R1 is labeled with an acceptor compound A1, and the receptor R2 is labeled with an energy acceptor compound A2. In the absence of the test compound, we can measure the luminescence L1 or L2 emitted at the emission wavelength of the acceptor compound A1 or A2, respectively. In this embodiment, the signal L1 is from the FRET emitted by the pair (D,A1) which labels the heterodimer R1R2, and the signal L2 is from the pairs (D,A2) which label the receptor R2, the homodimer R2R2, and the heterodimer R1R2. Depending on the specificity of binding of the test compound, the signal L2 will therefore be maintained, suppressed or decreased.

This other embodiment therefore makes it possible advantageously to establish whether the test compound is specific to the heterodimer R1R2 or whether it also binds to the receptor R2 or to the homodimer R2R2, or whether it is specific to the receptor R2 and to the homodimer R2R2, assuming that these species are present in the measuring medium.

According to this other embodiment of the second aspect of the invention, step (a) also comprises labeling of the receptor R2 covalently or noncovalently with a second energy acceptor compound A2, A1 and A2 having different emission wavelengths and (D,A2) forming a FRET partner pair, and step (c) also comprises measurement of the luminescence $L_2$ emitted at the emission wavelength of the acceptor compound A2, in the presence and in the absence of the test compound. According to this other embodiment:

a decrease of the luminescence L2 and disappearance of the luminescence L1 in the presence of the test compound are representative of the binding of this compound to the heterodimer R1R2, a decrease of the luminescence L2 and maintenance of the luminescence L1 in the presence of the test compound are representative of the binding of this compound to the receptor R2 and the homodimer R2R2 but not to the heterodimer R1R2, and disappearance of the signals L1 and L2 in the presence of the test compound is representative of the binding of this compound simultaneously to the receptor R2, the homodimer R2R2 and the heterodimer R1R2.

FRET Partner Pairs

According to the invention, the membrane receptors R1 and/or R2 as well as the ligand are labeled with a member of a FRET partner pair, namely, a fluorescent energy donor compound or a fluorescent energy acceptor compound. Advantageously, the labeling of the receptors R1 and R2 with the members of a FRET partner pair is direct labeling by covalent binding.

FRET is defined as a transfer of nonradiative energy resulting from a dipole-dipole interaction between an energy donor and an energy acceptor. This physical phenomenon requires energy compatibility between these molecules. This means that the emission spectrum of the donor must cover, at least partially, the absorption spectrum of the acceptor. In accordance with Förster's theory, FRET is a process that depends on the distance separating the two molecules, donor and acceptor: when these molecules are in close proximity to one another, a FRET signal will be emitted.

The fluorescent donor and acceptor compounds can be selected from the following group: allophycocyanins, in particular those known by the trade name XL665; luminescent organic molecules, such as rhodamines, cyanines (for example Cy5), squarains, coumarins, proflavins, acridines, fluoresceins, derivatives of boron-dipyrromethene (marketed under the designation "Bodipy"), fluorophores known by the name "Atto", fluorophores known by the name "Dy", compounds known by the name "Alexa", nitrobenzoxadiazole, fluorescent metal complexes, such as rare earth cryptates, rare earth chelates (in particular the chelates and cryptates of europium, of terbium, of samarium, of dysprosium, of neodymium); luminescent inorganic particles such as nanocrystals ("quantum dots"). These fluorescent compounds can be used either as fluorescent donor compounds or as fluorescent acceptor compounds in a FRET system.

Advantageously, the fluorescent acceptor compounds are selected from the allophycocyanins, the rhodamines, the cyanines, the squarains, the coumarins, the proflavins, the acridines, the fluoresceins, the derivatives of boron-dipyrromethene, and nitrobenzoxadiazole.

The expressions "the cyanines" and "the rhodamines" must be understood respectively as "the derivatives of cyanine" and "the derivatives of rhodamine". A person skilled in the art knows these various fluorophores, which are commercially available.

The compounds "Alexa" are marketed by the company Invitrogen; the compounds "Atto" are marketed by the company Attotec; the compounds "Dy" are marketed by the company Dyomics; the compounds "Cy" are marketed by the company Amersham Biosciences; the other compounds are marketed by various suppliers of chemical reagents, such as the companies Sigma, Aldrich or Acros.

The long-lived (>0.1 ms, preferably between 0.5 and 6 ms) fluorescent energy donor compounds, in particular the chelates or cryptates of rare earths are advantageous since they permit time resolved measurement, i.e. measurement of TR-FRET (Time Resolved FRET) signals while avoiding a high proportion of the background noise emitted by the measuring medium. For this reason, and generally, they are preferred for application of the method according to the invention. Advantageously, these compounds are complexes of lanthanides. These complexes (such as chelates or cryptates) are particularly suitable as energy donor member of the FRET pair.

The complexes of dysprosium (Dy3+), of samarium (Sm3+), of neodymium (Nd3+), of ytterbium (Yb3+) or of erbium (Er3+) are rare earth complexes that are also suitable for the purposes of the invention, but the complexes of europium (Eu3+) and of terbium (Tb3+) are particularly preferred.

Numerous rare earth complexes have been described and several are currently marketed by the companies PerkinElmer, Invitrogen and Cisbio Bioassay.

Examples of chelates or cryptates of rare earths suitable for the purposes of the invention are:

The cryptates of rare earths having one or more pyridine units. Rare earth cryptates of this kind are described for example in patents EP 0 180 492, EP 0 321 353, EP 0 601 113 and in international application WO 01/96 877. The cryptates of terbium (Tb3+) and of europium (Eu3+) are particularly suitable for the purposes of the present invention. Cryptates of rare earths are marketed by the company Cisbio Bioassay. We may mention, as nonlimiting examples, the cryptates of europium of the following formulas (which can be coupled to the compound to be labeled via a reactive group, here for example an NHS group):

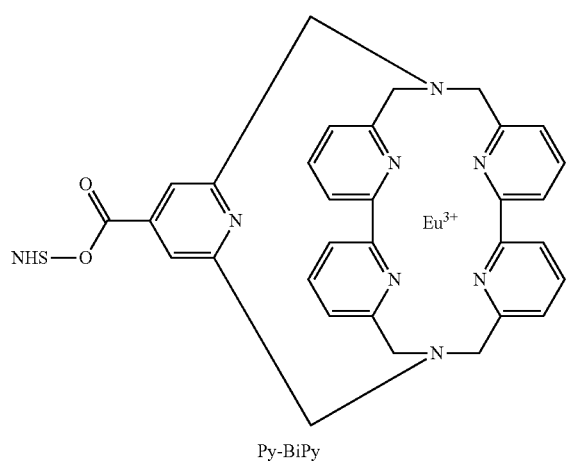

Py-BiPy

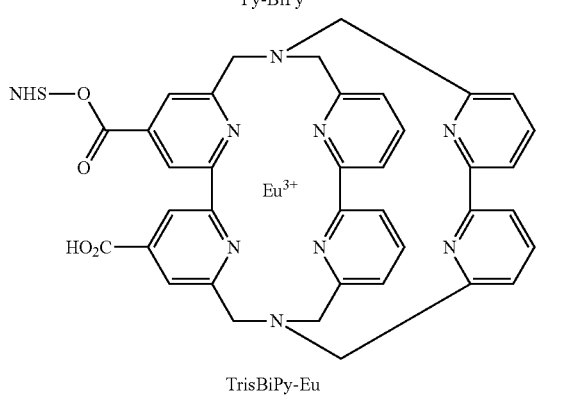

TrisBiPy-Eu

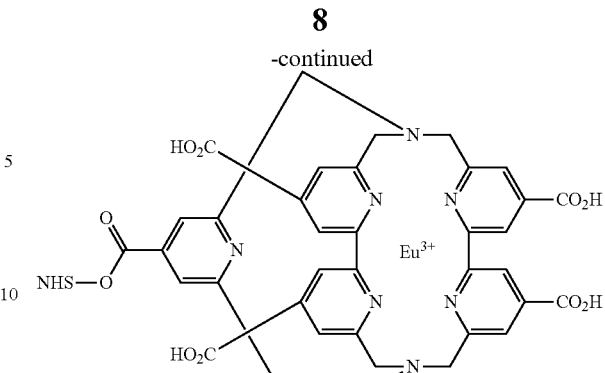

K-Py-BiPy-tetraacid-Eu

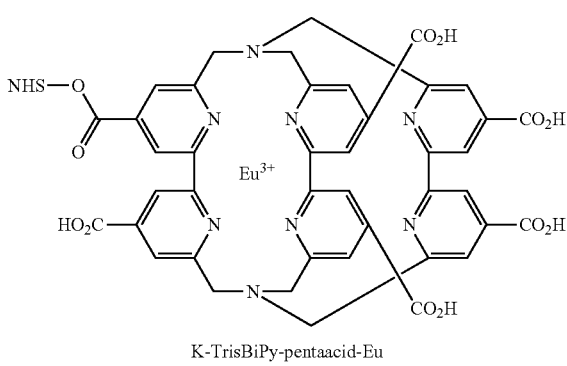

K-TrisBiPy-pentaacid-Eu

The europium cryptate Py-BiPy-tetraacid-Eu is particularly suitable for application of the invention owing to its properties of resistance to extinction of fluorescence in biological media.

The chelates of rare earths described notably in U.S. Pat. No. 4,761,481, U.S. Pat. No. 5,032,677, U.S. Pat. No. 5,055,578, U.S. Pat. No. 5,106,957, U.S. Pat. No. 5,116,989, U.S. Pat. No. 4,761,481, U.S. Pat. No. 4,801,722, U.S. Pat. No. 4,794,191, U.S. Pat. No. 4,637,988, U.S. Pat. No. 4,670,572, U.S. Pat. No. 4,837,159, U.S. Pat. No. 4,859,777. The patents EP 0 403 593, U.S. Pat. No. 5,324,825, U.S. Pat. No. 5,202,423, U.S. Pat. No. 5,316,909 describe chelates composed of a nonadentate ligand such as terpyridine. These chelates of rare earths are marketed by the company PerkinElmer.

Complexes of rare earths consisting of a chelating agent such as tetraazacyclododecane, substituted with a chromophore having aromatic rings, such as those described by Poole R. et al. in Biomol. Chem. 2005, 3, 1013-1024 "Synthesis and characterization of highly emissive and kinetically stable lanthanide complexes suitable for usage in cellulo", can also be used. The complexes described in application WO2009/10580 can also be used.

The terbium cryptate Tb(KR) of the following formula (which can be coupled to the compound to be labeled via a reactive group, here for example an NHS group):

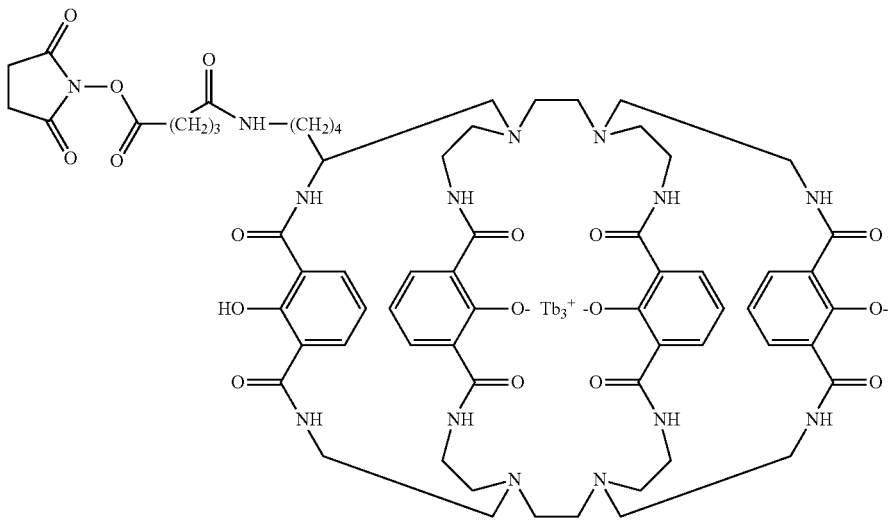

and the synthesis of which is described in international application WO2008/063721 is one of the most suitable terbium cryptates for application of the invention.

The terbium cryptate Lumi4-Tb from the company Lumiphore, marketed by Cisbio Bioassay, The "quantum dye" from the company Research Organics, of the following formula (which can be coupled to the compound to be labeled via a reactive group, here NCS):

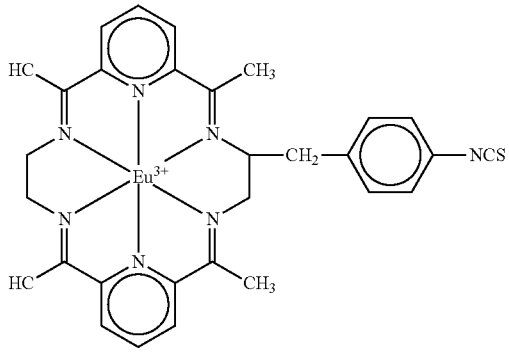

The terbium chelate DTPA-cs124 Tb, marketed by the company Invitrogen of the following formula (which can be coupled to the compound to be labeled via a reactive group R) and whose synthesis is described in U.S. Pat. No. 5,622,821.

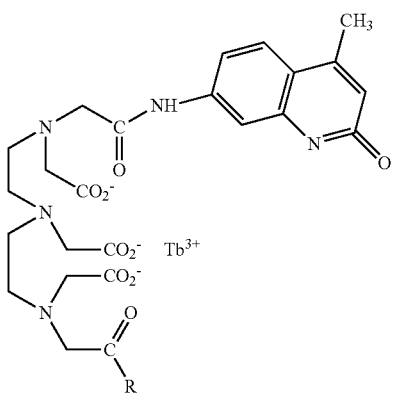

As for the acceptors, the derivatives of cyanine and of fluorescein are preferred.

Labeling of the Proteins R1 and/or R2

According to the invention, the membrane receptors R1 and/or R2 are labeled with a member of a FRET partner pair, namely a fluorescent energy donor compound or a fluorescent energy acceptor compound. Several techniques known by a person skilled in the art enable a membrane receptor to be coupled to fluorescent compounds:

(a) Coupling of the Membrane Receptor to a Donor or an Acceptor Noncovalently

The donor or acceptor can be coupled to the membrane receptor by means of a pair of binding partners, at least one of which is of protein nature. In this approach, the membrane receptor is fused with the binding partner of protein nature by the classical techniques of molecular biology (construction of an expression vector comprising a nucleotide sequence coding for the membrane receptor, fused with that coding for the protein binding partner, and introduction of the expression vector into the cell).

The donor or acceptor is conjugated covalently to the other binding partner, which is called coupling agent here, which will then be added to the extracellular medium. Recognition of the binding partners permits indirect labeling of the membrane receptor by the donor or the acceptor.

As nonlimiting examples of binding partners of this type, we may mention:

The pair consisting of the sequence cysteine-cysteine-X-X-cysteine-cysteine (SEQ ID No.1) in which X is any amino acid and of a bi-arsenic compound. These bi-arsenic compounds can easily be labeled with an organic molecule of the fluorescein or rhodamine type (see B. A. Griffin et al. (1998) Science, 1998, 281, 269-271 and S. A. Adams et al. (2002) J. Am. Chem. Soc. 2002, 124, 6063-6076 for details of the technology).

The peptide BTX (bungarotoxin), composed of 13 amino acids, which is recognized by bungarotoxin (BTX), can be coupled to a fluorescent molecule (see C. M. McCann et al, (2005), Biotechnique (2005), 38, 945-952).

The streptavidin (or avidin)/biotin pair: the binding sequence of streptavidin (SBP-Tag) is a sequence formed by 38 amino acids, which has a high affinity for biotin and can be labeled beforehand with a donor or an acceptor (see C. M. McCann et al. (2005), Biotechnique (2005), 38, 945-952).

The sequence of the enzyme dihydrofolate reductase of *E. coli* (eDHER) which binds specifically and with a high affinity for ligands, such as trimethoprim, on which the donor or the acceptor can be grafted according to the technology called "Ligand link Universal labeling technology" from the company Active Motif.

The tag/antitag pairs are binding partners often used for labeling proteins. The term "tag" denotes a small protein "label" consisting of an amino acid sequence, generally but not necessarily fairly short (less than 15 amino acids), which is fused to the membrane receptor or else is naturally present in this protein. The term "antitag" denotes an antibody that binds specifically to said "tag". In this application, the "antitag" antibody is bound covalently to the donor or to the acceptor. When the antibody labeled in this way is added to the extracellular medium, it binds to the "tag" conjugated to the membrane receptor and the "tag/antitag" interaction permits indirect labeling of this protein by the donor or the acceptor.

As nonlimiting examples of "tag/antitag" pairs, we may mention the following pairs, the members of which are available commercially: GST/anti-GST antibody in which GST represents glutathione S-transferase or a fragment thereof; 6HIS/anti-6HIS antibody in which 6HIS is a peptide consisting of 6 histidines; Myc/anti-Myc antibody in which Myc is a peptide consisting of the amino acids 410-419 of the human Myc protein; FLAG/anti-FLAG antibody in which FLAG is a peptide having the 8 amino acids DYKDDDDK (SEQ ID No.2); HA/anti-HA antibody in which HA is an epitope of the Influenza virus hemagglutinin, consisting of the 9 amino acids YPYDVPFYA (SEQ ID No.3). It is clear that the precise nature of the tag is not critical for application of the invention.

(b) Coupling of the Membrane Receptor to a Donor or an Acceptor Covalently

In this approach, the donor or the acceptor is coupled to the membrane receptor by a covalent bond; several techniques have been described and the reagents necessary for applying them are available commercially. For this coupling, one of the following techniques can be used:

formation of a covalent bond on a reactive group present on the membrane receptor, in particular on one of the following groups: terminal amino group, carboxylate groups of aspartic and glutamic acids, amine groups of lysines, guanidine groups of arginines, thiol groups of cysteines, phenol groups of tyrosines, indole rings of tryptophans, thioether groups of methionines, imidazole groups of histidines.

These groups present on the membrane receptor can form a covalent bond with a reactive group carried by the donor or the acceptor. The appropriate reactive groups are known by a person skilled in the art: a donor or the acceptor functionalized with a maleimide group will for example be capable of binding covalently with the thiol groups carried by the cysteines of the protein. Moreover, a donor/acceptor bearing an ester of N-hydroxysuccinimide will be capable of attaching covalently to an amine of the membrane receptor.

Use of a suicide enzyme

Suicide enzyme means proteins that have a n enzymatic activity modified by specific mutations which confer on them the capacity of binding a substrate rapidly and covalently. These enzymes are called "suicide" as each one can only bind a single fluorescent molecule, the activity of the enzyme being blocked by attachment of the substrate. These enzymes consequently constitute a tool of choice for specifically labeling receptors of interest with a ratio of one fluorescent molecule for one protein. In this approach, a suicide enzyme is fused, by the classical techniques of molecular biology, with the membrane receptor—preferably in its N-terminal portion—and the substrate of the enzyme bound covalently to a donor/acceptor is introduced into the extracellular medium. The enzymatic reaction leads to covalent binding of the substrate labeled with the enzyme, and therefore labeling of the membrane receptor by the donor or the acceptor.

We may mention, as nonlimiting examples, the following enzymes:

the mutants of O6-alkylguanine DNA alkyltransferase (AGT). The enzymes SNAP-tag (Juillerat et al., Chemistry & biology, Vol. 10, 313-317 April 2003) and CLIP-tag (Gautier et al., Chemistry and Biology, 15, 128-136, February 2008) marketed by the company NEB are mutants of human AGT, of which the substrates are, respectively, $O^6$-benzylguanine (abbreviated to BG hereinafter) and $O^2$-benzylcytosine (abbreviated to BC hereinafter). The enzyme N-AGT (Gronemeyer et al. (Protein engineering, design & selection, vol. 19, no 7, pp 309-3016, 2006)) is another mutant of this enzyme, whose reactivity with $O^6$-benzylguanine is better than that of the enzyme SNAP-tag.

the mutants of a dehalogenase (such as the enzyme HaloTag marketed by Promega) which also generates an enzymatic reaction of the suicide type (see WO2004/072232), certain substrates of which are compounds of the chloroalkane family, in particular the chloroalkanes having the unit —NH—$CH_2CH_2$—O—$CH_2CH_2$—O—$(CH_2)_6$—Cl. In this case, the donor/acceptor will be conjugated to this type of unit.

The protein ACP ("Acyl Carrier Protein"), on which the 4'-phosphopantetheine residue of coenzyme A is transferred, in the presence of phosphopantetheine transferase, onto a serine of the ACP (N. George et al., Journal of the American Chemical Society 126 (2004) p. 8896-8897). When this approach is used for labeling the membrane receptor with the donor or the acceptor, it is necessary to add phosphopantetheine transferase to the reaction mixture. The company NEB markets a fragment of ACP under the trade name "ACP-Tag" for labeling proteins.

When this approach is used for labeling the receptor of interest, the cells are transfected with an expression plasmid bearing the DNA coding for a fusion protein comprising the suicide enzyme and the receptor of interest. This plasmid can also comprise, upstream of the DNA coding for these proteins, the DNA coding for a label such as for example the epitope FLAG, the epitope myc, or that of the influenza virus hemagglutinin (HA). These labels are not essential but they facilitate manipulation of the fusion protein for purposes of checking or purification. Transfection is carried out by conventional techniques, such as electropartition.

To ensure that the fusion protein will be expressed in the cell membrane, it may be useful to include in the expression plasmid, upstream of the sequence coding for the receptor of interest and of the suicide enzyme, that coding for a membrane-addressing peptide, such as the signal peptide T8 or the signal peptide of the receptor mGluR5, use of which for this purpose is known by a person skilled in the art. Finally, it may also be desirable to ensure that the sequence coding for the receptor of interest does not bear a native membrane-addressing sequence, which could become the object of post-translational cleavage of the bond between the receptor of interest and the suicide enzyme: if this is the case, it is preferable not to introduce this domain into the expression plasmid.

When working on intact cells, so that the enzymatic reaction takes place with the substrate of the enzyme present in the extracellular medium (such as a BG-FRET partner conjugate), it is necessary for the suicide enzyme to be exposed to the extracellular medium: when the natural N-terminal portion of the receptor of interest is exposed to the extracellular medium, which is the case for GPCRs and RTKs, the fusion protein will be constructed in such a way that the suicide enzyme is expressed in the N-terminal portion of the fusion protein, but always downstream of the membrane-addressing peptide if it is present.

Finally, when a suicide enzyme is used for labeling the receptor of interest with the FRET partner, and the receptor of interest is a GPCR or RTK, the invention comprises a preliminary step of transfection of the cells by an expression vector comprising the DNA sequence coding for a fusion protein whose N-terminal portion comprises a suicide enzyme and C-terminal portion comprises the receptor of interest (R1 or R2).

The introduction of the substrate of the enzyme conjugated to a FRET partner in the extracellular medium will lead to labeling of the receptor of interest with this FRET partner.

Advantageously, each of the receptors R1 and R2 is expressed in the form of fusion protein with a suicide enzyme, labeling of them being effected by addition of the members of the FRET partner pairs to the measuring medium, each of which is bound covalently to the substrate of said suicide enzyme. In this case the suicide enzymes used for each receptor can be different or identical.

In this embodiment, the expression vectors coding for a fusion protein selected from the following fusion proteins can be used:

suicide enzyme—receptor of interest, or
label—suicide enzyme—receptor of interest, or
membrane-addressing peptide—suicide enzyme—receptor of interest, or
membrane-addressing peptide—label—suicide enzyme—receptor of interest.

As an illustration of the use of this approach, we may mention the works of Maurel et al., who described the preparation of plasmids coding for a fusion protein comprising a suicide enzyme (Snaptag) in the N-terminal portion of the membrane receptor (GABAB B1, GABAB B2, mGlu1) and their transfection in cells (Nature Methods, 2008, Supplementary methods).

Labeled Ligand

The method according to the invention requires the use of ligands of the membrane receptors under investigation, labeled with a member of a FRET partner pair, i.e. an energy donor compound or an energy acceptor compound. Here, the term ligand denotes an organic, optionally protein, molecule, capable of binding to the receptor and modulating its activity. The ligand is preferably different from an antibody, and even more preferably is an agonist (including a partial agonist or an inverse agonist) or an antagonist of the membrane receptors under investigation. It is also possible to use a ligand that is an allosteric modulator of these receptors.

Numerous ligands of GPCR have notably been described: a database has been made available to the public and supplies information on the GPCRs and their ligands (Okuno, Y. et al., 2008. GLIDA: GPCR ligand database for chemical genomics drug discovery database and tools update. *Nucl. Acids Res.*, 36(suppl_1), D907-912). A person skilled in the art therefore has access to a very large number of compounds that bind to GPCRs and can be used in the method according to the invention.

A ligand is labeled with a fluorescent donor or acceptor compound by the classical techniques of conjugation making use of reactive groups. The fluorescent donor or acceptor compounds are generally marketed in "functionalized" form, i.e. they bear a reactive group capable of reacting with a functional group present on the compound to be labeled, in this case the ligand.

Typically, the reactive group present on the fluorescent donor or acceptor compound is an electrophilic or nucleophilic group that can form a covalent bond when it is put in the presence of a suitable nucleophilic or electrophilic group, respectively. As examples, the pairs of electrophilic/nucleophilic groups and the type of covalent bond formed when they are brought together are listed below:

| Electrophilic group | Nucleophilic group | Type of bond |
|---|---|---|
| acrylamides | thiols | thioethers |
| acyl halides | amines/anilines | carboxamides |
| aldehydes | amines/anilines | imines |
| aldehydes or ketones | hydrazines | hydrazones |
| aldehydes or ketones | hydroxylamines | oximes |
| alkyl sulfonates | thiols | thioethers |
| anhydrides | amines/anilines | carboxamides |
| aryl halide | thiols | thiophenols |
| aryl halide | amines | aryl amines |
| aziridines | thiols | thioethers |
| carbodiimides | carboxylic acids | N-acylureas or anhydrides |
| activated esters* | amines/anilines | carboxamides |
| haloacetamides | thiols | thioethers |
| halotriazines | amines/anilines | aminotriazines |
| imido esters | amines/anilines | amidines |
| isocyanates | amines/anilines | ureas |
| isothiocyanates | amines/anilines | thioureas |
| maleimides | thiols | thioethers |
| sulfonate esters | amines/anilines | alkyl amines |
| sulfonyl halides | amines/anilines | sulfonamides |

*"activated ester" means groups of formula COY, where Y is: a leaving group, selected from the succinimidyloxy ($-OC_4H_4NO_2$), sulfosuccinimidyloxy ($-OC_4H_3NO_2-SO_3H$) groups; an aryloxy group, unsubstituted, or substituted with at least one electrophilic substituent such as the nitro, fluoro, chloro, cyano, trifluoromethyl groups, thus forming an activated aryl ester; a carboxylic acid activated by a carbodiimide group, forming an anhydride —OCORa or —OCNRaNHRb, in which Ra and Rb are identical or different and are selected from the C1-C6 alkyl, C1-C6 perfluoroalkyl, C1-C6 alkoxy, cyclohexyl groups; 3-dimethylaminopropyl, or N-morpholinoethyl.

The commercially available fluorescent donor and acceptor compounds generally bear a maleimide function or an activated ester, most often activated by an NHS (N-hydroxysuccinimidyl) group, which react with the thiol and amine groups respectively; it is therefore particularly advantageous to use ligands containing an amine or thiol function.

When the ligand is of protein nature, it may be advantageous to use one of the functional groups naturally present in proteins: the amino terminal group, carboxylate terminal group, carboxy late groups of aspartic and glutamic acids, amine groups of lysines, guanidine groups of arginines, thiol groups of cysteines, phenol groups of tyrosines, indole rings of tryptophans, thioether groups of methionines, imidazole groups of histidines.

If the ligand does not bear a functional group in the natural state, such groups can be introduced. Methods of introducing functional groups are notably described in C. Kessler, Nonisotopic probing, slotting and Sequencing, 2nd edition, L. J. Kricka (1995), Publ, Academic Press Ltd., London, p. 66-72.

Another approach for labeling a ligand with a fluorescent compound consists of introducing a reactive group into the ligand, for example an NHS group or a maleimide group, and of putting it in the presence of a fluorophore bearing a functional group that will react with the reactive group to form a covalent bond.

It is important to verify that the labeled ligand retains sufficient affinity for its receptor; this can be checked simply by conventional binding experiments, which allow the affinity constant of the labeled ligand for the receptor to be calculated.

Several authors have described the labeling of known ligands of GPCR with fluorescent compounds and it is within the capability of a person skilled in the art to select the appropriate ligands according to the GPCRs being investigated. We may mention in particular the following works:

Middleton, R. J. & Kellam, B., have published a review article describing numerous fluorescent ligands (2005, Fluorophore-tagged GPCR ligands. *Current Opinion in Chemical Biology*, 9(5), 517-525).

Beaudet, A. et al. have presented the essential principles for the preparation of fluorescent ligands (1998. Fluorescent ligands for studying neuropeptide receptors by confocal microscopy. *Brazilian Journal of Medical and Biological Research*, 31(11), 1479-1489).

Thierry Durroux et al. ("Fluorescent Pseudo-Peptide Linear Vasopressin Antagonists: Design, Synthesis, and Applications" Journal of Medicinal Chemistry 42, No, 7 Apr. 1, 1999: 1312-1319) described ligands of the receptor V1a, labeled with fluorescein.

International patent application WO00/12544 describes a method for labeling various chemokines, which are the ligands of the chemokine receptors.

International patent application WO2004/088312 describes the synthesis of agonists and of antagonists of β2-adrenergic receptors, labeled with a derivative of boron-dipyrromethene ("Bodipy"), L Hein et al. ("Intracellular trafficking of angiotensin II and its AT1 and AT2 receptors: evidence for selective sorting of receptor and ligand," Molecular Endocrinology (Baltimore, Md.) 11, No. 9 (August 1997): 1266-1277) synthesized an angiotensin-fluorescein conjugate.

U.S. Pat. No. 4,767,718 describes the synthesis of fluorescent ligands of the opioid receptors, in particular antagonists of these receptors derived from naloxone and naltrexone.

Heather L Handl et al. ("Lanthanide-based time-resolved fluorescence of in cyto ligand-receptor interactions," *Analytical Biochemistry* 330, No, 2 (Jul. 15, 2004): 242-250) present the manufacture of an analog of α-MSH, which is a ligand of the melacortin receptors, labeled with a europium chelate.

Bakthavachalam, V et al. described the labeling of ligands of the dopaminergic receptors D1 and D2 with fluorescein or with NBD, in particular NAPS (derivative of spiperone, D2 antagonist), PPHT (D1 agonist), SKF83566 (D1 antagonist), and SKF38393 (D1 agonist) (1991. Fluorescent probes for dopamine receptors: synthesis and characterization of fluorescein and 7-nitrobenz-2-oxa-1,3-diazol-4-yl conjugates of D-1 and D-2 receptor ligands. *Journal of Medicinal Chemistry*, 34(11), 3235-3241).

As nonlimiting examples of ligands usable in the methods according to the invention, we may add the following ligands:

EDA9 (antagonist of the V2 receptor, synthesis of which is described by Manning, M. et al., 1992. Potent V2/V1a vasopressin antagonists with C-terminal ethylenediamine-linked retro-amino acids. *Journal of Medicinal Chemistry*, 35(21), 3895-3904), NAPS (antagonist of the D2 receptor), RS544 (antagonist of the V1a receptor), SDF1 (agonist of CXCR4 and CXCR7), Propranolol (antagonist of the beta2-adrenergic receptors), VIP (agonist of VPAC1 and of VPAC2), NDPalphaMSH (agonist of the MC3 and MC4 receptors), MIP1alpha (inflammatory protein of macrophages=CCL3, agonist of CCR1 and CCR5), RANTES (=CCL5, agonist of CCR5), MDC (=CCL22, agonist of CCR4), Angiotensin II (agonist of the receptor of AT1), Substance P (agonist of the NK1 receptor), Neurokinin A (agonist of the NK2 receptor).

Moreover, some fluorescent ligands are commercially available: this applies for example to naloxone-fluorescein (opioid antagonist), which is marketed by Molecular Probe. Cisbio bioassays also markets a wide range of fluorescent ligands of membrane receptors suitable for application of the invention, in particular fluorescent derivatives of prazosin (antagonist of the alpha adrenergic receptor), propranolol (antagonist of the beta 2 adrenergic receptor), angiotensin II (agonist of the AT1 and AT2 receptor), HOE140 (antagonist of the bradykinin B2 receptor), SDF1alpha (agonist of CXCR4), cholecystokinin (agonist of the receptor CCK1, CCK2), spiperone and NAPS (antagonists of the dopaminergic D2 receptor), CGP 54626 (antagonist of the GA BAB receptor), ghrelin (antagonist of the GHSR1A receptor), GIP ("Gastric inhibitory polypeptide", agonist of the GIPR receptor), mepyramine (inverse agonist of the histamine receptor H1), MSH ("melanocyte stimulating hormone", agonist of the melanocortin receptors MC3, MC4, MC5), naltrexone (antagonist of the mu, delta and kappa opioid receptors), substance P (agonist of the neurokinin receptors NK1), neurokinin A (agonist of the neurokinin receptor NK2), a specific agonist of VPAC1 that does not bind to VPAC2, argininevasopressin (antagonist of the receptors V1a and V2).

These ligands can be used when R1 and/or R2 are one of the membrane receptors to which these ligands bind.

Thus, EDA9 conjugated to a fluorescent compound is useful for applying the invention with the heterodimers V1a-V2, V2-OT, D2-V2 or the V2-V2 homodimer.

NAPS or spiperone conjugated to a fluorescent compound is useful for applying the invention with the heterodimers D2-A1, D2-A2A, D2-SSTR5, D2-D3, D2-SSTR1B, D2-CCR4, D2-CCR3, D2-CCR1, D2-NK1, D2-NK2, D2-AT1, D2-MC3, D2-MC4, D2-Mu Opioid, D2-GHSR1a, D2-ETA, D2-ETB, D2-CCK1, D2-CCK2, D2-VPAC1, D2-VPAC2, D2-β2AR, D2-CXCR4, D2-CXCR7, D2-V2 and the D2-D2 homodimers.

RS544 conjugated to a fluorescent compound is useful for applying the invention with the heterodimers V1a-V2, V1a-OT, and the V1a-V1a homodimers.

Naltrexazone conjugated to a fluorescent compound is useful for applying the invention with the heterodimers μ-opioid-SSTR1A, κ-opioid-δ-opioid, μ-opioid-δ-opioid, δ-opioid-α2aAR, δ-opioid-SSTR2A, δ-opioid-NK1-P, δ-opioid-β2AR, μ-opioid-D2 and the homodimers μ-opioid-μ-opioid and δ-opioid-δ-opioid.

Substance P conjugated to a fluorescent compound is useful for applying the invention with the heterodimers NK1-δ-opioid, NK1-D2.

Angiotensin II conjugated to a fluorescent compound is useful for applying the invention with the heterodimers AT2-β2AR, AT2-B2, AT2-AT1, AT1-D2.

RANTES conjugated to a fluorescent compound is useful for applying the invention with the heterodimers CCR5-CCR2 and the homodimers of CCR5.

Propranolol conjugated to a fluorescent compound is useful for applying invention with the heterodimers β2AR-AT2, β2AR-δ-opioid, β2AR-κ-opioid, β2AR-Y1, β2AR-H2, β2AR-M3, β2AR-5HT2B, β2AR-5HT2C, β2AR-H3, β2AR-EP1, β2AR-β3AR, β2ARα2aAR, β2AR-M71, β2AR-D2 and the β2AR-β2AR homodimers.

SDF1 conjugated to a fluorescent compound is useful for applying the invention with the heterodimers CXCR4-CCR2, CXCR4-CCRA32, CXCR4-CXCR2B, CXCR4-D2 and the CXCR4CXCR4 homodimers.

Membrane Protein: Monomers, Dimers, Homodimers and Heterodimers

The invention can be applied with various membrane receptors but, preferably, the membrane receptors R1 and R2 are GPCRs.

The membrane receptors are expressed in the cell membranes naturally, or else they are expressed using the classical techniques of molecular biology, in particular expression vectors introduced into the cells stably or transiently. The reagents intended for introduction of heterologous DNA into cells, stably or transiently, are commercially available and the DNA sequences coding for the receptors of interest, in particular those coding for the GPCRs, are available in databases such as Genbank. When the receptors of interest are expressed by the cells stably, phenomena of cytotoxicity may be observed owing to the presence of an excessive number of GPCRs; in these cases, it may be advantageous to use an inducible expression system to limit expression of the GPCRs.

Thus, the method according to the invention can comprise a preliminary step of transfection of cells with an expression vector coding for the membrane receptor R1 and/or R2. As described below, this vector/these vectors can also contain the sequences coding for suicide enzymes permitting the covalent labeling of the membrane receptors with a FRET partner. In particular, transfection of the cells is effected by means of an expression vector comprising the DNA sequence coding for the receptor R1 on the one hand, and by an expression vector comprising the DNA sequence coding for the receptor R2 on the other hand, Preferably the receptors R1 and R2 are each expressed by an expression vector introduced into the cell stably or transiently.

The invention is particularly suitable for investigating the pharmacology of the GPCRs. A list of the known GPCRs has been published and the DNA sequences coding for these receptors are also accessible (Harmar A J et al, (2009) IUPHAR-DB: the IUPHAR database of G protein-coupled receptors and ion channels, Nucl. Acids Res. 37 (Database issue): D580-D585). This list, summarized in Table 1, also gives the known natural ligands of these receptors.

TABLE 1

| Family | Natural ligand | IUPHAR official name |
|---|---|---|
| Receptors of 5-hydroxytryptamine | 5-hydroxytryptamine | 5-HT1A |
| | 5-hydroxytryptamine | 5-HT1B |
| | 5-hydroxytryptamine | 5-HT1D |
| | 5-hydroxytryptamine | 5-ht1e |
| | 5-hydroxytryptamine | 5-HT1F |
| | 5-hydroxytryptamine | 5-HT2A |
| | 5-hydroxytryptamine | 5-HT2B |
| | 5-hydroxytryptamine | 5-HT2C |
| | 5-hydroxytryptamine | 5-HT4 |
| | 5-hydroxytryptamine | 5-ht5a |
| | 5-hydroxytryptamine | 5-HT6 |
| | 5-hydroxytryptamine | 5-HT7 |
| Acetylcholine (muscarinic) receptors | acetylcholine | M1 |
| | acetylcholine | M2 |
| | acetylcholine | M3 |
| | acetylcholine | M4 |
| | acetylcholine | M5 |
| Adenosine receptors | adenosine | A1 |
| | adenosine | A2A |
| | adenosine | A2B |
| | adenosine | A3 |
| Adrenergic receptors | noradrenaline | α1A-adrenoceptor |
| | adrenaline | α1B-adrenoceptor |
| | adrenaline | α1D-adrenoceptor |
| | adrenaline | α2A-adrenoceptor |
| | adrenaline | α2B-adrenoceptor |
| | adrenaline | α2C-adrenoceptor |
| | noradrenaline | β1-adrenoceptor |
| | adrenaline | β2-adrenoceptor |
| | adrenaline | β3-adrenoceptor |
| Anaphylatoxin receptors | anaphylatoxin C5a, C5a of Arg74 | C5L2 |
| | anaphylatoxin C5a | C5a |
| | anaphylatoxin C3a | C3a |
| Angiotensin receptors | angiotensin | AT1 |
| | angiotensin | AT2 |
| Apelin receptors | apelin | APJ |
| Bile acid receptors | bile acids | GPBA |
| Bombesin receptors | neuromedin B | BB1 |
| | gastrin-releasing peptide | BB2 |
| | | BB3 |
| Bradykinin receptors | bradykinin | B1 |
| | bradykinin | B2 |
| Cannabinoid receptors | cannabinoids | CB1 |
| | cannabinoids | CB2 |
| Chemokine receptors | CXCL8 | CXCR1 |
| | CXCL1-3, CXCL5-8, macrophage derived lectin | CXCR2 |
| | CXCL9-11 | CXCR3 |
| | CXCL12 | CXCR4 |
| | CXCL13 | CXCR5 |
| | CCL3, CCL5, CCL7, CCL8, CCL13-16, CCL23 | CCR1 |
| | CCL2, CCL7, CCL8, CCL13 | CCR2 |
| | CCL11 (eotaxin); CCL5, CCL7, CCL8, CCL13, CCL15, CCL24, CCL26 | CCR3 |
| | CCL17, CCL22 | CCR4 |
| | CCL3, CCL4, CCL5, CCL8, CCL14 | CCR5 |
| | CCL20 | CCR6 |
| | CCL19, CCL21 | CCR7 |
| | CCL1, CCL4, CCL17 | CCR8 |
| | CCL25 | CCR9 |
| | CCL26-28 | CCR10 |
| | CX3CL1 | CX3CR1 |
| | XCL1, XCL2 | XCR1 |
| | CXCL16 | CXCR6 |
| Cholecystokinin receptors | cholecystokinin | CCK1 |
| | cholecystokinin, gastrin | CCK2 |
| Dopamine receptors | dopamine | D1 |
| | dopamine | D2 |
| | dopamine | D3 |
| | dopamine | D4 |
| | dopamine | D5 |
| Endothelin receptors | endothelin 1, endothelin 2 | ETA |
| | endothelins 1, 2 and 3 | ETB |
| Estrogen receptors (coupled to G proteins) | | GPER |
| Formylpeptide receptors | | FPR2/ALX |
| | | FPR3 |
| | | FPR1 |
| Receptors of free fatty acids | Long-chain carboxylic acids | FFA1 |
| | | FFA3 |
| | | FFA2 |
| | | GPR42 |

TABLE 1-continued

GPCRs

| Family | Natural ligand | IUPHAR official name |
|---|---|---|
| Galanin receptors | galanin | GAL1 |
|  | galanin | GAL2 |
|  | galanin | GAL3 |
| Ghrelin receptors | ghrelin | ghrelin |
| Receptors of glycoprotein hormones | follicle-stimulating hormone | FSH |
|  | luteinizing hormone, chorionic gonadotropin | LH |
|  | thyroid-stimulating hormone | TSH |
| Gonadoliberin receptors | gonadoliberin | GnRH |
|  | gonadoliberin | GnRH2 |
| Histamine receptors | histamine | H1 |
|  | histamine | H2 |
|  | histamine | H3 |
|  | histamine | H4 |
| KiSS1-derived peptide receptors |  | KiSS1 |
| Leukotriene receptors | leukotriene B4 | BLT2 |
|  |  | FPR2/ALX |
|  | 5-oxo-ETE | OXE |
|  | leukotriene B4 | BLT1 |
|  | leukotriene D4 | CysLT1 |
|  | leukotriene C4 | CysLT2 |
| Lysophospholipid receptors | lysophosphatidic acid | LPA1 |
|  | lysophosphatidic acid | LPA2 |
|  | lysophosphatidic acid | LPA3 |
|  | sphingosine 1-phosphate | S1P1 |
|  | sphingosine 1-phosphate | S1P2 |
|  | sphingosine 1-phosphate | S1P3 |
|  | sphingosine 1-phosphate | S1P4 |
|  | sphingosine 1-phosphate | S1P5 |
| Receptors of melanin concentrating hormone |  | MCH1 |
|  |  | MCH2 |
| Melanocortin receptors | melanocyte stimulating hormone | MC1 |
|  | adrenocorticotropic hormone | MC2 |
|  | γ-melanocyte stimulating hormone | MC3 |
|  | β-melanocyte stimulating hormone | MC4 |
|  | α-melanocyte stimulating hormone | MC5 |
| Melatonin receptors | melatonin | MT1 |
|  | melatonin | MT2 |
| Motilin receptor | motilin | motilin |
| Neuromedin U receptors | neuromedin U | NMU1 |
|  | neuromedin U | NMU2 |
| Receptors of neuropeptide FF/neuropeptide AF |  | NPFF1 |
|  |  | NPFF2 |
| Neuropeptide S receptor |  | NPS |
| Receptors of neuropeptide W/neuropeptide B |  | NPBW1 |
|  |  | NPBW2 |
| Neuropeptide Y receptors | neuropeptide Y | Y1 |
|  | neuropeptide Y | Y2 |
|  | pancreatic polypeptide | Y4 |
|  | neuropeptide Y | Y5 |
| Neurotensin receptors | neurotensin | NTS1 |
|  | neurotensin | NTS2 |
| Nicotinic acid receptors | nicotinic acid (low affinity) | GPR109B (temporary name) |
|  | nicotinic acid (high affinity) | GPR109A (temporary name) |
|  | lactate | GPR81 (temporary name) |
| Non-signalling 7TM chemokine-binding proteins |  | FY |
|  |  | CCPB2 |
|  |  | CCRL1 |
| Opioid receptors | β-endorphin | μ |
|  | β-endorphin | δ |
|  | dynorphin A | K |
|  | nociceptin/orphanin FQ | NOP |
| Orexin receptors | orexin A, orexin B | OX1 |
|  | orexin A, orexin B | OX2 |
| P2Y receptors | ADP | P2Y1 |
|  | UTP, ATP | P2Y2 |
|  | UTP | P2Y4 |
|  | UDP | P2Y6 |
|  | ATP | P2Y11 |
|  | ADP | P2Y12 |
|  | UDP-glucose | P2Y14 |
|  | ADP | P2Y13 |
| Receptor of peptide P518 | RF-amide P518 gene product | QRFP |
| Platelet-activating factor receptor | platelet-activating factor | PAF |
| Prokineticin receptors |  | PKR1 |
|  |  | PKR2 |
| Prolactoliberin receptors |  | PRRP |
| Prostanoid receptors | prostaglandin D2 | DP1 |
|  | prostaglandin E2 | EP1 |
|  | prostaglandin E2 | EP2 |
|  | prostaglandin E2 | EP3 |
|  | prostaglandin E2 | EP4 |
|  | prostaglandin F2a | FP |
|  | prostacyclin | IP1 |
|  | thromboxane A2 | TP |
|  | 11-dehydro-thromboxane B2 | DP2 |
| Protease-activated receptors | thrombin | PAR1 |
|  | serine protease | PAR2 |
|  | thrombin | PAR3 |
|  | serine protease | PAR4 |
| Receptors of peptides of the relaxin family |  | RXFP1 |
|  |  | RXFP2 |
|  |  | RXFP3 |
|  |  | RXFP4 |
| Somatostatin receptors | somatostatin | sst2 |
|  | somatostatin | sst5 |
|  | somatostatin | sst3 |
|  | somatostatin | sst1 |
|  | somatostatin | sst4 |
| Receptors of tachykinin | substance P | NK1 |
|  | neurokinin A | NK2 |
|  | neurokinin B | NK3 |
| Thyroliberin receptor | thyrotropin-releasing hormone | TRH1 |
| Receptor of trace amines |  | TA1 |
| Urotensin receptor | urotensin II | UT |
| Receptors of vasopressin and of oxytocin | vasopressin | V1A |
|  | vasopressin | V2 |
|  | vasopressin | V1B |
|  | oxytocin | OT |
| Olfactory receptors |  |  |
| Calcitonin receptors | amylin, CGRP | CT |
|  |  | AMY1 |
|  |  | AMY2 |
|  |  | AMY3 |
|  | adrenomedullin, CGRP | CALCRL |
|  |  | CGRP |
|  |  | AM1 |
|  |  | AM2 |

TABLE 1-continued

GPCRs

| Family | Natural ligand | IUPHAR official name |
|---|---|---|
| Corticoliberin receptors | | CRF1 |
| | | CRF2 |
| Glucagon receptors | glucagon | glucagon |
| | | GLP-1 |
| | | GLP-2 |
| | | GIP |
| | secretin | secretin |
| | | GHRH |
| Parathyroid hormone receptors | parathyroid hormone | PTH1 |
| | TIP-39 | PTH2 |
| Receptors of VIP and of PACAP | PACAP | PAC1 |
| | VIP, PACAP | VPAC1 |
| | VIP, PACAP | VPAC2 |
| Calcium-sensing receptors | calcium | CaS |
| | | GPRC6 |
| GABAB receptors | GABAB | GABAB1 |
| | | GABAB2 |
| | | GABAB |
| GPRC5 receptors | | RAIG1 |
| | | RAIG2 |
| | | RAIG3 |
| | | RAIG4 |
| Metabotropic glutamate receptors | glutamate | mGlu1 |
| | glutamate | mGlu2 |
| | glutamate | mGlu3 |
| | glutamate | mGlu4 |
| | glutamate | mGlu5 |
| | glutamate | mGlu6 |
| | glutamate | mGlu7 |
| | glutamate | mGlu8 |
| Taste receptors | | T1R1 |
| | | T1R2 |
| | | T1R3 |
| "Frizzled" receptors | Wnt3A, Wnt3, Wnt1, Wnt2 | FZD1 |
| | Wnt | FZD2 |
| | Wnt | FZD3 |
| | Wnt | FZD4 |
| | Wnt | FZD5 |
| | Wnt | FZD6 |
| | Wnt | FZD7 |
| | Wnt | FZD8 |
| | Wnt | FZD9 |
| | Wnt | FZD10 |
| | constitutive | SMO |

Table 2 gives examples of GPCR heterodimers consisting of a first receptor R1 and a second receptor R2. These heterodimers can be used in the methods according to the invention.

TABLE 2

| R1 is a GPCR | | | R2 is a GPCR | | |
|---|---|---|---|---|---|
| | class | type | | class | type |
| MgluR2 | C | metabo Glu | MgluR3 | C | metabo Glu |
| MgluR2 | C | metabo Glu | MgluR4 | C | metabo Glu |
| MgluR2 | C | metabo Glu | MgluR8 | C | metabo Glu |
| MgluR3 | C | metabo Glu | MgluR4 | C | metabo Glu |
| MgluR3 | C | metabo Glu | MgluR8 | C | metabo Glu |
| MgluR4 | C | metabo Glu | MgluR8 | C | metabo Glu |
| MgluR1 | C | metabo Glu | CaS | C | calcium sensing |
| MgluR1 | C | metabo Glu | A1 | A | adenosine |
| MgluR2 | C | metabo Glu | 5-HT2A | A | serotonin |
| MgluR5 | C | metabo Glu | A2A | A | adenosine |
| GABAB1 | C | GABAB | GABAB2 | C | GABAB |
| 5-HT1B | A | serotonin | 5-HT1D | A | serotonin |
| A1 | A | adenosine | D1 | A | dopamine |
| A1 | A | adenosine | D2 | A | dopamine |
| A1 | A | adenosine | P2Y1 | A | purinergic |
| A2A | A | adenosine | D2 | A | dopamine |
| A2A | A | adenosine | D3 | A | dopamine |
| AT1 | A | angiotensin | AT2 | A | angiotensin |
| AT1 | A | angiotensin | B2 | A | bradykinin |
| AT2 | A | angiotensin | β2AR | A | B2-adrenoceptor |
| AT2 | A | angiotensin | B2 | A | bradykinin |
| M2 | A | muscaranic AchI | M3 | A | muscaranic AchI |
| MT1 | A | melatonin | MT2 | A | melatonin |
| SSTR2A | A | somatostatin | SSTR1B | A | somatostatin |
| SSTR2A | A | somatostatin | SSTR1B | A | somatostatin |
| D2 | A | dopamine | SSTR5 | A | somatostatin |
| D2 | A | dopamine | D3 | A | dopamine |
| D1 | A | dopamine | D2 | A | dopamine |
| CCR2 | A | chemokine | CCR5 | A | chemokine |
| SSTR1A | A | somatostatin | μ-opioid | A | opioid |
| SSTR1A | A | somatostatin | SSTR1C | A | somatostatin |
| SSTR1 | A | somatostatin | SSTR5 | A | somatostatin |
| SSTR1B | A | somatostatin | D2 | A | dopamine |
| SSTR2 | A | somatostatin | SSTR3 | A | somatostatin |
| T1R1 | C | taste | T1R3 | C | taste |
| T1R2 | C | taste | T1R3 | C | taste |
| δ-opioid | A | opioid | K-opioid | A | opioid |
| μ-opioid | A | opioid | δ-opioid | A | opioid |
| δ-opioid | A | opioid | α2aAR | A | A2-adrenoceptor |
| δ-opioid | A | opioid | SSTR2A | A | somatostatin |
| δ-opioid | A | opioid | NK1-P | A | tachykinin |
| δ-opioid | A | opioid | β2AR | A | B2-adrenoceptor |
| δ-opioid | A | opioid | SNSR4 | A | |
| K-opioid | A | opioid | β2AR | A | B2-adrenoceptor |
| Orexin1 | A | orexin | CB1 | A | cannabinoid |
| MT1 | A | melatonin | GPR50 | ? | Orph |
| MrgE | ? | Orph | MrgD | ? | Orph |
| ETA | A | endothelin | ETB | A | endothelin |
| V1a | A | vasopressin | V2 | A | vasopressin |
| V1a | A | vasopressin | OT | A | oxytocin |
| V2 | A | vasopressin | OT | A | oxytocin |
| α1aAR | A | A1-adrenoceptor | α1bAR | A | A1-adrenoceptor |
| α1bAR | A | A1-adrenoceptor | H1 | A | histamine |
| α1dAR | A | A1-adrenoceptor | α1bAR | A | A1-adrenoceptor |
| β1AR | A | B1-adrenoceptor | α2aAR | A | A2-adrenoceptor |
| β1AR | A | B1-adrenoceptor | β2AR | A | B2-adrenoceptor |
| β2AR | A | B2-adrenoceptor | M71 | A | olfactory receptor |
| β2AR | A | B2-adrenoceptor | α2aAR | A | A2-adrenoceptor |
| β2AR | A | B2-adrenoceptor | B3AR | A | B3-adrenoceptor |
| β2AR | A | B2-adrenoceptor | EP1 | A | |
| β2AR | A | B2-adrenoceptor | H3 | A | histamine |
| β2AR | A | B2-adrenoceptor | 5HT2C | A | serotonin |
| β2AR | A | B2-adrenoceptor | 5HT2B | A | serotonin |
| β2AR | A | B2-adrenoceptor | M3 | A | muscaranic AchI |
| β2AR | A | B2-adrenoceptor | H2 | A | histamine |
| β2AR | A | B2-adrenoceptor | Y1 | A | neuropeptide Y |
| 5HT2C | A | serotonin | β3AR | A | B3-adrenoceptor |
| 5HT2C | A | serotonin | Y5 | A | neuropeptide Y |
| 5HT2C | A | serotonin | M1 | A | muscaranic AchI |
| CXCR1 | A | chemokine | CXCR2 | A | chemokine |
| CXCR4 | A | chemokine | CXCR2B | A | chemokine |
| CXCR4 | A | chemokine | CCRΔ32 | A | chemokine |
| CXCR4 | A | chemokine | CCR2 | A | chemokine |
| CCR2 | A | chemokine | CCR5 | A | chemokine |
| D2 | A | dopamine | CCR1 | A | chemokine |
| D2 | A | dopamine | CCR3 | A | chemokine |

TABLE 2-continued

| R1 is a GPCR | | | R2 is a GPCR | | |
|---|---|---|---|---|---|
| | class | type | | class | type |
| D2 | A | dopamine | CCR4 | A | chemokine |
| D2 | A | dopamine | NK1 | A | tachykinin |
| D2 | A | dopamine | NK2 | A | tachykinin |
| D2 | A | dopamine | AT1 | A | angiotensin |
| D2 | A | dopamine | MC3 | A | melanocortin |
| D2 | A | dopamine | MC4 | A | melanocortin |
| D2 | A | dopamine | μ-opioid | A | opioid |
| D2 | A | dopamine | GHSR1a | A | ghrelin |
| D2 | A | dopamine | ETA | A | endothelin |
| D2 | A | dopamine | ETB | A | endothelin |
| D2 | A | dopamine | CCK1 | A | cholecystokinin |
| D2 | A | dopamine | CCK2 | A | cholecystokinin |
| D2 | A | dopamine | VPAC1 | B | VIP, PACAP |
| D2 | A | dopamine | VPAC2 | B | VIP, PACAP |
| D2 | A | dopamine | β2AR | A | B2-adrenoceptor |
| D2 | A | dopamine | CXCR4 | A | chemokine |
| D2 | A | dopamine | CXCR7 | A | chemokine |
| D2 | A | dopamine | V2 | A | vasopressin |

The GPCRs in Table 3 can form homodimers.

TABLE 3

| GPCR | class | type |
|---|---|---|
| CaSR | C | calciumSensing |
| MgluR1 | C | metabo Glu |
| MgluR2 | C | metabo Glu |
| MgluR3 | C | metabo Glu |
| MgluR4 | C | metabo Glu |
| MgluR5 | C | metabo Glu |
| MgluR6 | C | metabo Glu |
| MgluR7 | C | metabo Glu |
| MgluR8 | C | metabo Giu |
| 5-HT2C | A | serotonin |
| 5-HT1B | A | serotonin |
| 5-HT1C | A | serotonin |
| β1AR | A | B1-adrenoceptor |
| β2AR | A | B2-adrenoceptor |
| V1a | A | vasopressin |
| V2 | A | vasopressin |
| δ-opioid | A | opioid |
| μ-opioid | A | opioid |
| k-opioid | A | opioid |
| D1 | A | dopamine |
| D2 | A | dopamine |
| D3 | A | dopamine |
| H2 | A | histamine |
| H4 | A | histamine |
| α2aAR | A | A2-adrenoceptor |
| B4 | A | bradykinin |
| B2 | A | bradykinin |
| CCR2 | A | chemokine |
| CCR5 | A | chemokine |
| CXCR4 | A | chemokine |
| CXCR2 | A | chemokine |
| CXCR1 | A | chemokine |
| CCK | A | cholecystokinin |
| LTB1 | A | leukotriene |
| MT1 | A | melatonin |
| MT2 | A | melatonin |
| M2 | A | muscarinic Achl |
| M3 | A | muscarinic Achl |
| OT | A | oxytocin |
| SSTR5 | A | somatostatin |
| SSTR1A | A | somatostatin |
| SSTR1B | A | somatostatin |
| SSTR1C | A | somatostatin |
| SSTR2A | A | somatostatin |
| GnRH | A | gonadotrophin |
| TRH | B | thyrotropin |
| GHSR1 | A | ghrelin |
| IgGhepta | B | |
| A1 | A | adenosine |

TABLE 3-continued

| GPCR | class | type |
|---|---|---|
| PACAP | B | |
| PAR1 | A | thrombin |
| AT1 | A | angiotensin |
| Rhodopsin | A | |
| Frizzled4 | | |
| MC1 | A | melacortin |

EXAMPLES

Example1

Preparation of Cells Expressing Monomers and Homodimers of V2 Receptors, Fused with a Suicide Enzyme SNAPtag (ST) or CLIPtag (CT)

Reagent and Material Used:
OptiMEM (Invitrogen (51985-026))
Krebs-glucose: Krebs buffer+glucose 0.5 g/l
FLAG-ST-V2 plasmid: plasmid bearing the sequence coding for a fusion protein comprising a membrane-addressing signal peptide T8, the FLAG epitope, the enzyme SNAPTAG and the V2 receptor. The sequence of this plasmid is SEQ ID No.4.
FLAG-CT-V2 plasmid: plasmid bearing the sequence coding for a fusion protein comprising a membrane-addressing signal peptide T8, the FLAG epitope, the enzyme CLIPTAG and the V2 receptor. The sequence of this plasmid is identical to that of the FLAG-ST-V2 plasmid apart from the sequence coding for SNAPtag, which has been replaced with that coding for CLIPtag. A vector bearing the enzyme CLIP-tag is marketed by the company New England biolabbs (NEB), which also supplies its sequence.
Treatment of the Plates
50 μl of solution of poly-L-ornithine (0.01% solution, molecular weight 30,000-70,000 (SIGMA P4957)) was distributed in each well of a 96-well plate (Cellstar, black with black bottom) to promote adherence of the cells to the bottom of the well, and the plates were incubated for 30 min at 37° C.
Transfection
The following transfection mixture was then distributed in each well:
  0.16 μg of plasmid FLAG-ST-V2+0.16 μg of plasmid FLAG-CT-V2
  0.8 μl of Lipofectamine 2000
  50 μl of OptiMEM medium
After incubation for 30 minutes, 100 μl of a suspension containing 100 000 cells COS7 was added to each well, then incubated for 24 hours at 37° C. in the presence of 5% $CO_2$.

Example 2

Preparation of Cells Expressing Monomers of Receptors mGlu3, mGlu2, and Heterodimers of Receptors mGlu2-mGlu3

The same protocol as in example 1 was used for expression of heterodimers mGluR2-mGluR3, using the same plasmids as in this example but replacing the sequence of the V2 receptor with that of the mGlu2 or mGlu3 receptor. Thus, the plasmids FLAG-ST-mGluR2 and FLAG-ST-mGluR3 were used for expression of the dimers mGluR2-mGluR3, in which mGluR2 is fused to SNAPtag and mGluR3 is fused to CLIPtag.

Example 3

Cells Expressing the Dopamine D2 Receptor and the Delta Opioid Receptor 3.1 Reagents:

So-called complete medium: DMEM Glutamax™-L, 10% fetal calf serum, 1% MEM NEAA (Non-Essential Amino Acids), 1% Pen-Strep, 2 mM HEPES. Supplier: Gibco (Invitrogen).

Opti MEM Glutamax™-L marketed by Gibco.

Tag-Lite® buffer: marketed by Cisbio bioassays.

Tag-Lite® SNAP-Lumi4Tb: Substrate of the enzyme SNAP-Tag, marketed by Cisbio Bioassays. This reagent can be used here for labeling the receptor SNAPTag-Delta Opioid.

Tag-Lite® Halo-Lumi4Tb: Substrate of the enzyme Halo-Tag, marketed by Cisbio Bioassays. This reagent can be used here for labeling the receptor HaloTag-Dopamine D2.

Red antagonist of the dopamine D2 receptor: Ligand of the Dopamine D2 receptor (Spiperone derivative), coupled to a red acceptor fluorophore. Marketed by Cisbio ("*Opioid receptor red antagonist*", Ref. L0002RED).

Red antagonist of the opioid receptor: Ligand of the Delta Opioid receptor (naltrexone derivative), coupled to a red acceptor fluorophore Marketed by Cisbio ("*Opioid receptor red antagonist*", Ref. L0005RED).

Antagonists, Agonists, Inverse Agonists specific to the Dopamine D2 receptor: NAPS (antagonist) supplied by Columbia University, New York; Bromocriptine (partial agonist), Spiperone (antagonist), Haloperidol (inverse agonist), (S)-(−)-Sulpiride (inverse agonist) marketed by Tocris; PPHT (agonist) from Sigma. These six compounds are each taken up in a solution containing 100% of dimethylsulfoxide (DMSO, Sigma), except for the NAPS which is resolubilized in 10% DMSO and 90% water.

Antagonists, Agonists, Inverse Agonists specific to the Delta Opiold receptor: Endomorphin I (agonist) resolubilized in 100% $H_2O$, Naltrindole (antagonist) taken up in 100% DMSO, SNC-162 (agonist) resolubilized in $H_2O$+1 equivalent HCl. Naloxone (Antagonist) resolubilized in 90% $H_2O$ and 10% DMSO. These compounds are marketed by Tocris.

Flag-SNAP-Delta Opioid Plasmid; plasmid bearing the sequence coding for a fusion protein comprising a membrane-addressing signal peptide 18, the FLAG epitope, the enzyme SNAPTAG and the Delta Opioid receptor. The sequence of this plasmid is SEQ ID No.5.

Flag-Halo-Dopamine D2 Plasmid: plasmid bearing the sequence coding for a fusion protein comprising a membrane-addressing signal peptide T8, the FLAG epitope, the enzyme Halotag and the dopamine D2 receptor. The sequence of this mid is SEQ ID No.6.

3.2 Cell Cultures:

Adherent HEK293T/17 cells were cultured with 25 ml of complete culture medium, in Easy Flask T175 flasks (Nuns), at 37° C. under humid atmosphere at 5% $CO_2$. The cells were detached from the flask, from which the culture medium had been removed beforehand, using 5 ml of cell dissociation buffer (Gibco). The density and the viability of the cells were evaluated using a Vi-Cell™-XR cell counter (Beckman Coulter).

3.3. Transient Transfection and Labeling:

50 µl of solution of poly-L-ornithine (0.01% solution, molecular weight 30,000-70,000 (SIGMA P4957)) was distributed in each well of a 96-well plate (Cellstar, black with black bottom) in order to promote adherence of the cells to the bottom of the well, and the plates were incubated for 20 min at 37° C.

The following transfection mixture was prepared, for each well:
- 48.5 µl of OptiMEM medium preheated to 37° C.
- 0.35 µg of Flag-SNAP-Delta Opioid plasmid+0.35 µg of Flag-Halo-Dopamine D2 plasmid
- 0.8 µl of Lipofectamine 2000

After vortexing and incubation for 30 minutes at room temperature, this mixture was deposited in each well of the plate, after aspiration of the poly-L-ornithine, and at a rate of 50 µl per well.

100 µL of a suspension of HEK293T cells at a concentration of 1 million/ml (prepared in 3.2) was then added to each well, i.e. 100 000 cells per well. The plate was then incubated for 24 h at 37° C. under humid atmosphere at 5% $CO_2$.

After the 24 h of incubation, the medium in each well was aspirated, 100 µL of a solution of SNAP-Lumi4Tb or HALO-Lumi4Tb at 100 nM was then added to each well, to label the receptors with the fluorescent substrates, by reaction with the Snaptag or Halotag domains of the fusion proteins. The plate was then incubated at 37° C. for 1 h, then rinsed by four successive washings with 100 µl per well of Tag-Lite® buffer. Finally, 50 µl of this buffer was added to each well.

3.4. Determination of the Affinity of the Fluorescent Reference Ligands on the Delta Opioid—D2 Heterodimer The affinity of the fluorescent reference ligands for the heterodimers was determined by incubating the cells at room temperature with increasing concentrations of fluorescent ligand. For each concentration of fluorescent ligand, the non-specific binding signal is determined by adding an excess of nonfluorescent ligand (10 µM of NAPS for Dopamine D2 and 10 µM of Naltrindole for delta Opioid). The fluorescent and nonfluorescent ligands were diluted in Tag-lite buffer. 25 µl of nonfluorescent ligand or of Tag-lite buffer was added to the plates prepared in example 3.3, followed by addition of 25 µl of fluorescent ligand. The plates were then incubated at room temperature for 3 h before signal detection.

The signal was measured at 665 nm and 620 nm on a Rubystar reader (BMG Labtech). The HTRF ratio was then calculated by dividing the signal of the acceptor (665 nm) by that of the donor (620 nm) and multiplying this value by 10 000. The results were then analyzed on GraphPad Prism (GraphPad Software, Inc., San Diego, Calif.). The dissociation constants (Kd) of the fluorescent ligands were obtained from the saturation curves of the specific binding signal. The specific binding signal was obtained by subtracting the non-specific HTRF ratio from the total HTRF ratio.

Figure 8:
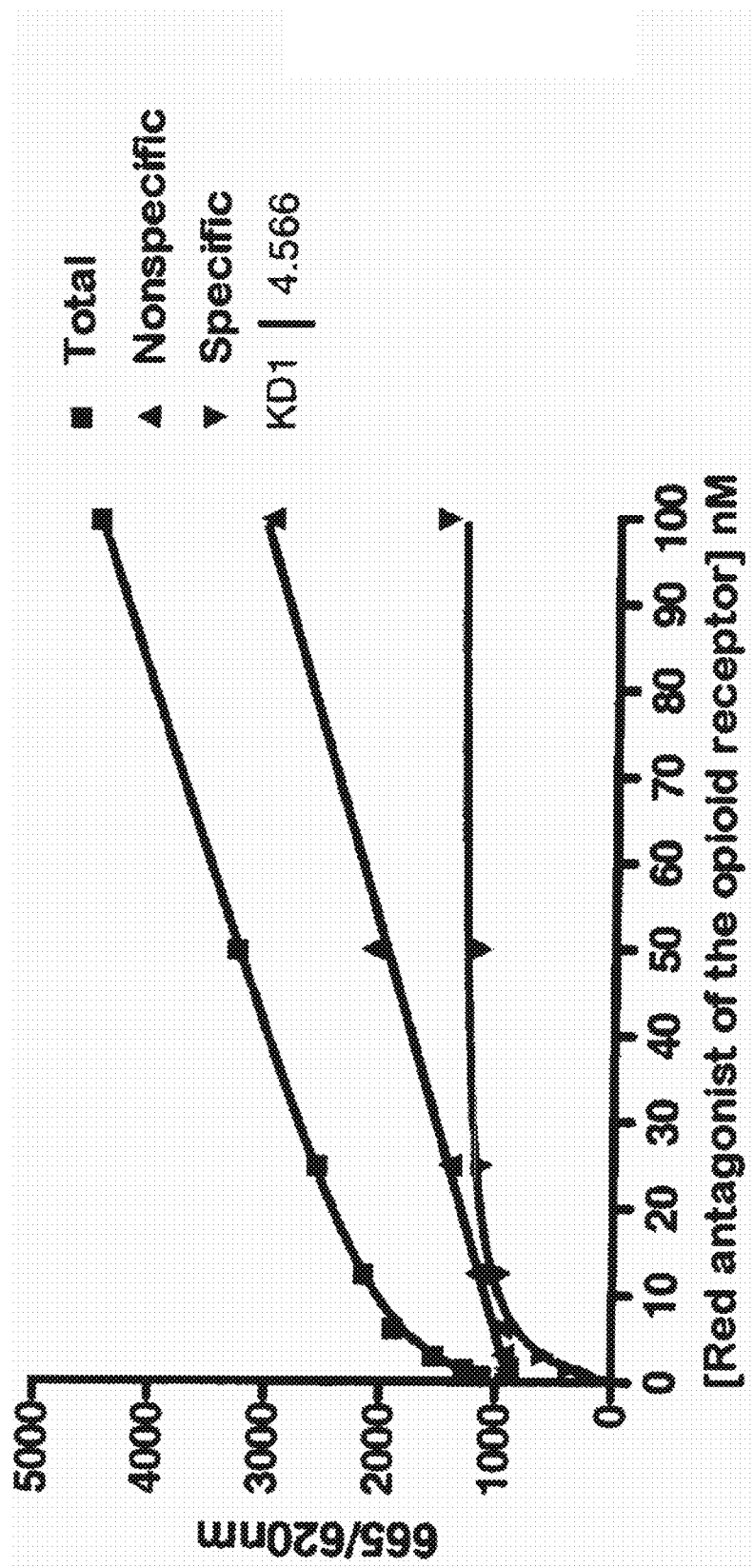
FIG. 8 represents determination of the dissociation constant of the opioid receptor red antagonist on the Delta Opioid receptor of the Delta Opioid/Dopamine D2 heterodimer. The dopamine D2 receptor is labeled with HALO-Lumi4Tb thus permitting visualization of fixation of the fluorescent ligand on the heterodimer.

FIG. 8 corresponds to the dose-response curve obtained by measuring the signal emitted by cells whose D2 receptor has been labeled with HALO-Lumi4Tb, in the presence of increasing concentration of red antagonist of the opioid receptor. The Kd of the red antagonist of the opioid receptor for the Delta Opioid receptor implicated in a heterodimer is 4.57 nM.

Figure 9:
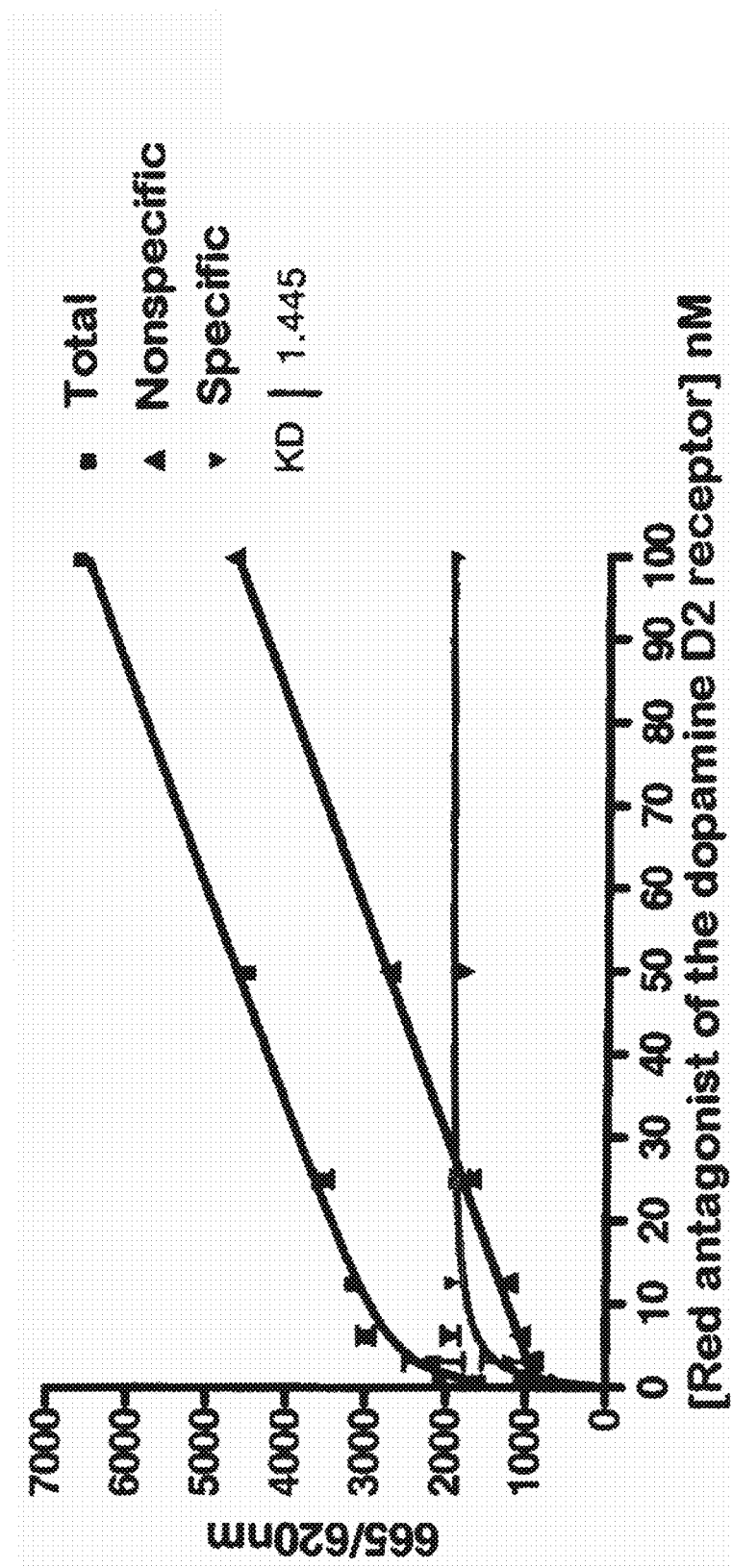
FIG. 9 represents determination of the dissociation constant of the red antagonist of the dopamine D2 receptor on the Dopamine D2 receptor of the Delta Opioid/Dopamine D2 heterodimer. The Delta Opioid receptor is labeled with SNAP-Lumi4Tb thus permitting visualization of fixation of the fluorescent ligand on the heterodimer.

FIG. 9 corresponds to the dose-response curve obtained by measuring the signal emitted by cells whose Delta Opioid receptor has been labeled with SNAP-Lumi4Tb, in the presence of increasing concentration of red antagonist of the dopamine D2 receptor. The Kd of the red antagonist of the D2 receptor for the D2 receptor implicated in a heterodimer is 1.44 nM.

3.5. Investigation of the Pharmacology of Various Compounds on the Heterodimers of Delta Opioid—D2 Receptors Competitive tests between the fluorescent ligands at fixed concentrations (3 nM of the red antagonist of the dopamine D2 receptor or of the opioid receptor) and of the test compounds at increasing concentrations, enabled us to evaluate the affinity of these compounds for the heterodimers.

The fluorescent ligands and the test compounds were diluted in Tag-lite buffer. 25 µl of the test compound or of Tag-lite buffer was added to the plates prepared in example 3.3, followed by addition of 25 µl of fluorescent ligand. The plates were then incubated at room temperature for 3 h before signal detection.

The signal was measured at 665 nm and 620 nm on a Rubystar reader (BMG Labtech). The HTRF ratio was then calculated by dividing the signal of the acceptor (665 nm) by that of the donor (620 nm) and multiplying this value by 10 000. The results were then analyzed on GraphPad Prism (GraphPad Software, Inc., San Diego, Calif.). The values of the inhibition constants (Ki) of the compounds were obtained from the competitive tests using the equation of Cheng and Prusoff.

Figure 10:
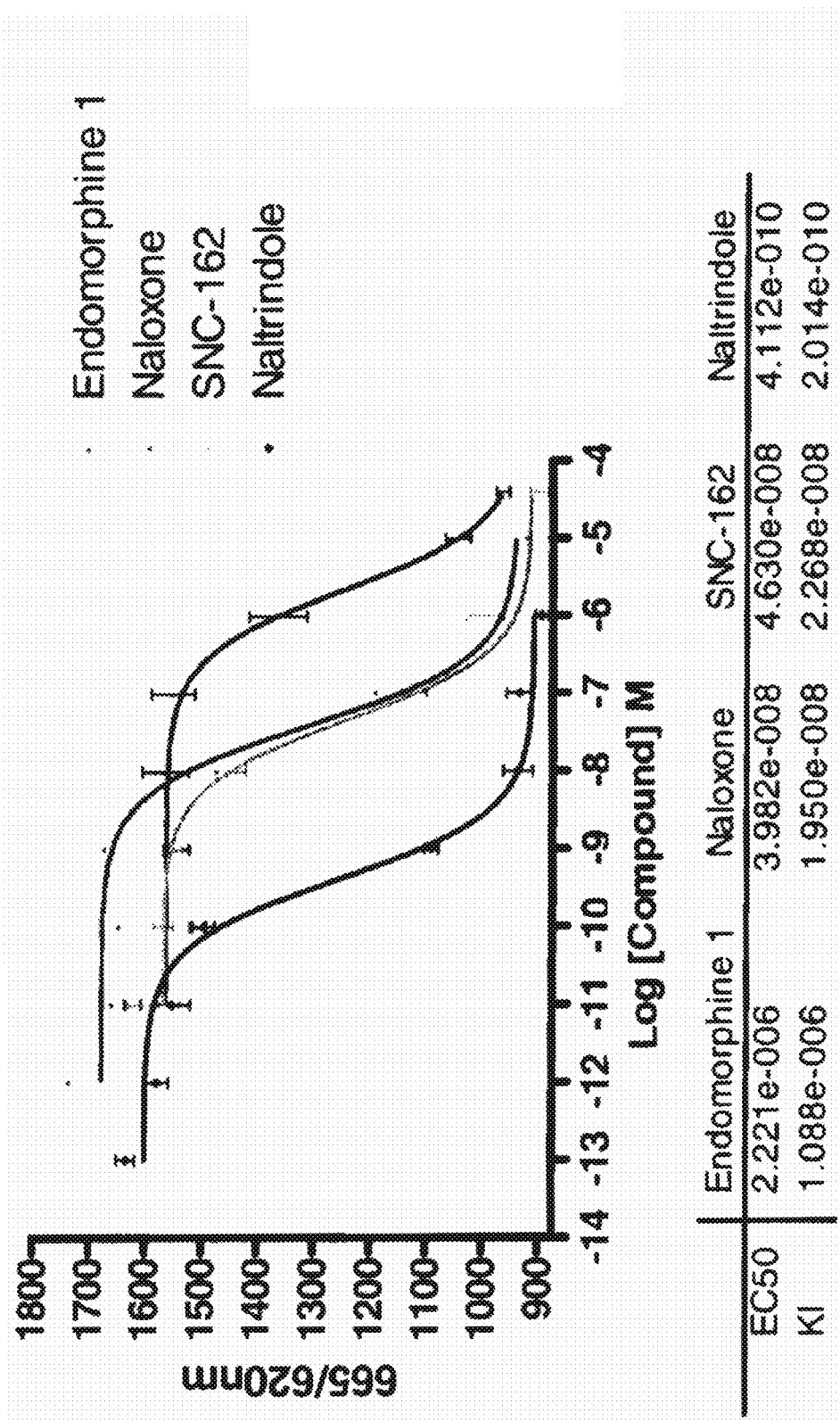
FIG. 10 represents screening of specific compounds of the Delta Opioid receptor implicated in the heterodimer with Dopamine D2. The Dopamine D2 receptor is labeled with HALO-Lumi4Tb thus permitting visualization of competition specifically on the heterodimers.

FIG. 10 shows the variation of the signal emitted by cells whose D2 receptor had been labeled with HALO-Lumi4Tb, in the presence of a fixed concentration of red antagonist of the opioid receptor, and of increasing concentration of various test compounds (Endomorphin 1, Naloxone, SNC-162 and Naltrindole). The curves obtained show that the test compounds compete with the fluorescent reference ligand and bind to the heterodimers. This figure also shows the Ki values calculated for each of the compounds tested.

Figure 11:
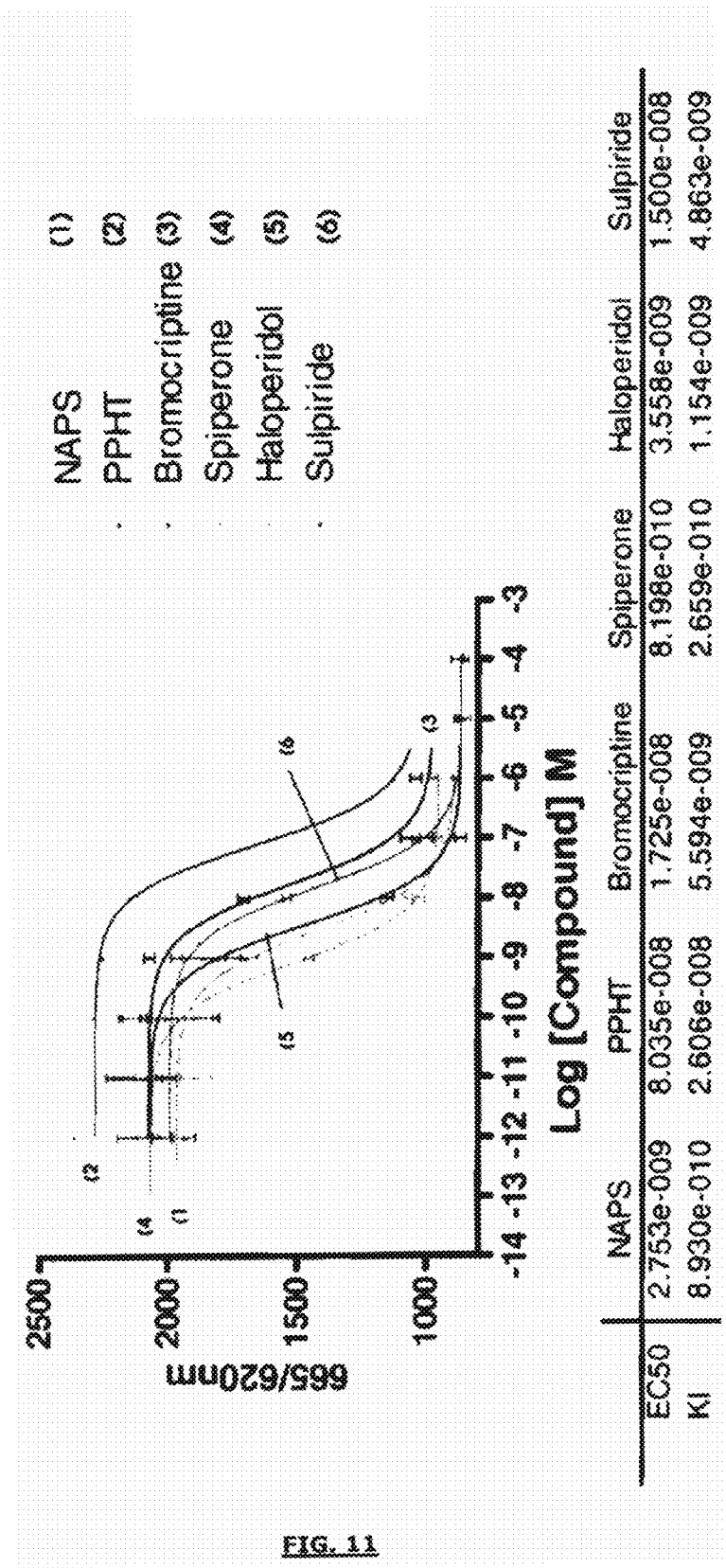
FIG. 11 represents screening of specific compounds of the Dopamine D2 receptor implicated in the heterodimer with Delta Opioid. The Delta Opioid receptor is labeled with SNAP-Lumi4Tb thus permitting visualization of competition on the Dopamine D2 receptors of the heterodimers.

FIG. 11 shows the variation of the signal emitted by cells whose Delta opioid receptor had been labeled with SNAP-Lumi4Tb, in the presence of a fixed concentration of red antagonist of the dopamine D2 receptor, and of increasing concentration of various test compounds (NAPS, PPHT, Bromocriptine, Spiperone, Haloperidol and Sulpiride). The curves obtained show that the test compounds compete with the fluorescent reference ligand and bind to the heterodimers. This figure also shows the Ki values calculated for each of the compounds tested.

The invention claimed is:

1. A method for determining the binding of a test compound to membrane receptors R1 and R2 expressed on the surface of cells, wherein the receptors R1 and R2 are known to be expressed in a heterodimeric form, the method comprising the steps of:
    (a) labelling the receptor R1 covalently or noncovalently with a first member of a FRET partner pair (D,A1), in which D is an energy donor compound and A1 is an energy acceptor compound;
    (b) adding, to a measuring medium, a known ligand of the receptor R2 that is capable of binding to a heterodimer R1R2 but neither to the receptor R1 nor to a homodimer R1R1, said ligand being labelled with a second member of said FRET partner pair, and said ligand being selected from: a known agonist compound of the receptor R2, a known antagonist compound of the receptor R2 or a known allosteric modulator of the receptor R2; and
    (c) measuring a luminescence $L_1$ emitted at an emission wavelength of the energy acceptor compound $A_1$ in the presence or in the absence of the test compound;
    wherein the receptor R1 is expressed in the form of a fusion protein with a suicide enzyme, and is labelled by adding to the measuring medium said first member of the FRET partner pair (D,A1) covalently bonded to a substrate of said suicide enzyme.

2. The method of claim 1, wherein the first member of said FRET partner pair that is used for labelling the receptor R1 is the energy donor compound D, and the second member of said FRET partner pair that is bonded to the ligand is the energy acceptor compound A1.

3. The method of claim 1, wherein the first member of said FRET partner pair that is used for labelling the receptor R1, is the energy acceptor compound A1, and the second member of said FRET partner pair that is bonded to the ligand is the energy donor compound D.

4. The method of claim 3, wherein step (a) further comprises labelling the receptor R2 covalently or noncovalently with a second energy acceptor compound A2, A1 and A2 having different emission wavelengths and (D,A2) forming a FRET partner pair, wherein the receptor R2 is expressed in the form of a fusion protein with a suicide enzyme, and is labelled by adding to the measuring medium said second energy acceptor A2 that is covalently bonded to the substrate of said suicide enzyme, and wherein step (c) further comprises measuring the luminescence $L_2$ emitted at an emission wavelength of the energy acceptor compound A2, in the presence or in the absence of the test compound.

5. The method of claim 1, wherein the receptors R1 and R2 are G protein-coupled receptors.

6. The method of claim 1, wherein the energy donor compounds are fluorescent complexes of lanthanides.

7. The method of claim 6, wherein the fluorescent complexes of lanthanides are fluorescent complexes of terbium or fluorescent complexes of europium.

8. The method of claim 4, wherein each of the receptors R1 and R2 is expressed in the form of a fusion protein with a suicide enzyme that is different from that of the other.

9. The method of claim 4, wherein each of the receptors R1 and R2 is expressed in the form of a fusion protein with a suicide enzyme that is the same as that of the other.

10. The method of claim 4, which further comprises a preliminary step of transfecting the cells with an expression vector comprising a DNA sequence encoding the receptor R1, and with an expression vector comprising a DNA sequence encoding the receptor R2.

11. The method of claim 10, wherein each of the expression vectors comprises a DNA sequence encoding a fusion protein, wherein an N-terminal portion of the fusion protein comprises a suicide enzyme and a C-terminal portion of the fusion protein comprises the receptor R1 or R2.

12. The method of claim 1, which further comprises a step of comparing the values of luminescence $L_1$ measured in the absence and in the presence of the test compound.

13. The method of claim 1, which further comprises a preliminary step of transfecting the cells with an expression vector comprising a DNA sequence encoding the receptor R1.

14. The method of claim 13, wherein the expression vector comprises a DNA sequence encoding a fusion protein, wherein an N-terminal portion of the fusion protein comprises a suicide enzyme and a C-terminal portion of the fusion protein comprises the receptor R1.

15. A method for determining the binding of a test compound to membrane receptors R1 and R2 expressed on the surface of cells, wherein the R1 and R2 receptors are known to be expressed in a heterodimeric form, the method comprising the steps of:
(a) labelling the receptor R1 covalently or noncovalently with a first member of a FRET partner pair (D,A1), in which D is an energy donor compound and A1 is an energy acceptor compound;
(b) adding, to the measuring medium, a known ligand of the receptor R2 that is capable of binding to the heterodimer R1R2 but neither to the receptor R1 nor to a homodimer R1R1, said ligand being labelled with a second member of said FRET partner pair (D,A1), and said ligand being selected from: a known agonist compound of the receptor R2, a known antagonist compound of the receptor R2 or a known allosteric modulator of the receptor R2;
(c) measuring the luminescence $L_1$ emitted at an emission wavelength of the energy acceptor compound $A_1$, in the presence or in the absence of the test compound;
wherein the receptor R1 is expressed in the form of a fusion protein with a suicide enzyme, and is labelled by adding to the measuring medium said first member of the FRET partner pair (D,A1) that is covalently bonded to a substrate of said suicide enzyme; and
wherein the receptor R2 is expressed in the form of a fusion protein with a suicide enzyme, and is labelled by adding to the measuring medium, a second energy acceptor A2 that is covalently bonded to a substrate of said suicide enzyme, A1 and A2 having different emission wavelengths and (D,A2) forming a FRET partner pair.

16. The method of claim 15, wherein each of the receptors R1 and R2 is expressed in the form of a fusion protein with a suicide enzyme that is different from that of the other.

17. The method of claim 15, wherein each of the receptors R1 and R2 is expressed in the form of a fusion protein with a suicide enzyme that is the same as that of the other.

18. The method of claim 15, which further comprises a preliminary step of transfecting the cells with an expression vector comprising a DNA sequence encoding the receptor R1 on the one hand, and with an expression vector comprising a DNA sequence encoding the receptor R2 on the other hand.

19. The method of claim 18, wherein each of the expression vectors comprises a DNA sequence encoding a fusion protein, wherein an N-terminal portion of the fusion protein comprises a suicide enzyme and a C-terminal portion of the fusion protein comprises the receptor R1 or R2.

20. The method of claim 15, further comprising comparing the values of luminescence $L_1$ measured in the absence and in the presence of the test compound.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: artificial sequence
<220> FEATURE:
<223> OTHER INFORMATION: binding partner
<220> FEATURE:
<221> NAME/KEY: MISC_FEATURE
<222> LOCATION: (3)..(4)
<223> OTHER INFORMATION: Xaa is any amino acid

<400> SEQUENCE: 1

Cys Cys Xaa Xaa Cys Cys
1               5

<210> SEQ ID NO 2
<211> LENGTH: 8
<212> TYPE: PRT
<213> ORGANISM: artificial sequence
<220> FEATURE:
<223> OTHER INFORMATION: tag/antitag pair

<400> SEQUENCE: 2

Asp Tyr Lys Asp Asp Asp Asp Lys
1               5

<210> SEQ ID NO 3
<211> LENGTH: 9
<212> TYPE: PRT
<213> ORGANISM: artificial sequence
<220> FEATURE:
<223> OTHER INFORMATION: tag/antitag pair

<400> SEQUENCE: 3

Tyr Pro Tyr Asp Val Pro Phe Tyr Ala
1               5

<210> SEQ ID NO 4
<211> LENGTH: 7154
<212> TYPE: DNA
<213> ORGANISM: artificial sequence
```

```
<220> FEATURE:
<223> OTHER INFORMATION: plasmid
<220> FEATURE:
<221> NAME/KEY: misc_feature
<222> LOCATION: (232)..(819)
<223> OTHER INFORMATION: CMV promoter
<220> FEATURE:
<221> NAME/KEY: misc_feature
<222> LOCATION: (923)..(986)
<223> OTHER INFORMATION: T8 leader sequence
<220> FEATURE:
<221> NAME/KEY: misc_feature
<222> LOCATION: (1004)..(1027)
<223> OTHER INFORMATION: QC tag
<220> FEATURE:
<221> NAME/KEY: misc_feature
<222> LOCATION: (1046)..(1591)
<223> OTHER INFORMATION: Snap tag
<220> FEATURE:
<221> NAME/KEY: misc_feature
<222> LOCATION: (1598)..(2710)
<223> OTHER INFORMATION: gene of interest
<220> FEATURE:
<221> NAME/KEY: misc_feature
<222> LOCATION: (2754)..(2978)
<223> OTHER INFORMATION: BGH polyA
<220> FEATURE:
<221> NAME/KEY: misc_feature
<222> LOCATION: (3862)..(4656)
<223> OTHER INFORMATION: Neo R
<220> FEATURE:
<221> NAME/KEY: misc_feature
<222> LOCATION: (6158)..(7018)
<223> OTHER INFORMATION: Ampi R

<400> SEQUENCE: 4
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg    780
gtaggcgtgt acggtggag gtctatataa gcagagctct ctggctaact agagaaccca    840
ctgcttactg gcttatcgaa attaatacga ctcactatag ggagacccaa gctggctagc    900
gtttaaactt aagctttgag acatggcctt accagtgacc gccttgctcc tgccgctggc    960
cttgctgctc cacgccgcca ggccggccgc cgctagcggc atcgactaca aggacgacga   1020
tgacaaggcc ggcatcgatg ccatcatgga caaagactgc gaaatgaagc gcaccaccct   1080
ggatagccct ctgggcaagc tggaactgtc tgggtgcgaa cagggcctgc acgagatcaa   1140
gctgctgggc aaaggaacat ctgccgccga cgccgtgaa gtgcctgccc agccgccgt    1200 gctgggcgga ccagagccac tgatgcaggc caccgcctgg ctcaacgcct actttcacca   1260
gcctgaggcc atcgaggagt ccctgtgtgc cagccctgcac cacccagtgt ccagcagga   1320
```

-continued

```
gagctttacc cgccaggtgc tgtggaaact gctgaaagtg gtgaagttcg agaggtcat    1380
cagctaccag cagctggccg ccctggccgg caatcccgcc gccaccgccg ccgtgaaaac    1440
cgccctgagc ggaaatcccg tgcccattct gatccctgc caccgggtgg tgtctagctc    1500
tggcgccgtg gggggctacg agggcgggct cgccgtgaaa gagtggctgc tggcccacga    1560
gggccacaga ctgggcaagc ctgggctggg tgatatcctc atggcgtcca ccacttccgc    1620
tgtgcctggg catccctctc tgcccagcct gcccagcaac agcagccagg agaggccact    1680
ggacacccgg gacccgctgc tagcccgggc ggagctggcg ctgctctcca tagtctttgt    1740
ggctgtggcc ctgagcaatg gcctggtgct ggcggccta gctcggcggg gccggcgggg    1800
ccactgggca cccatacacg tcttcattgg ccacttgtgc ctggccgacc tggccgtggc    1860
tctgttccaa gtgctgcccc agctggcctg gaaggccacc gaccgcttcc gtgggccaga    1920
tgccctgtgt cgggccgtga agtatctgca gatggtgggc atgtatgcct cctcctacat    1980
gatcctggcc atgacgctgg accgccaccg tgccatctgc cgtcccatgc tggcgtaccg    2040
ccatggaagt ggggctcact ggaaccggcc ggtgctagtg gcttgggcct tctcgctcct    2100
tctcagcctg ccccagctct tcatcttcgc ccagcgcaac gtggaaggtg gcagcggggt    2160
cactgactgc tgggcctgct tgcggagcc ctggggccgt cgcacctatg tcacctggat    2220
tgccctgatg tgtgttcgtgg cacctaccct gggtatcgcc gcctgccagg tgctcatctt    2280
ccgggagatt catgccagtc tggtgccagg gccatcagag aggcctgggg ggcgccgcag    2340
gggacgccgg acaggcagcc ccggtgaggg agcccacgtg tcagcagctg tggccaagac    2400
tgtgaggatg acgctagtga ttgtggtcgt ctatgtgctg tgctgggcac ccttcttcct    2460
ggtgcagctg tgggccgcgt gggacccgga ggcacctctg gaagggggcgc ctttgtgct    2520
actcatgttg ctggccagcc tcaacagctg caccaacccc tggatctatg catctttcag    2580
cagcagcgtg tcctcagagc tgcgaagctt gctctgctgt gcccggggac gcaccccacc    2640
cagcctgggt ccccaagatg agtcctgcac caccgccagc tcctccctgg caaggacac    2700
ttcatcgtga ctcgagtcta gagggccgt ttaaacccgc tgatcagcct cgactgtgcc    2760
ttctagttgc cagccatctg ttgtttgccc ctccccgtg ccttccttga ccctggaagg    2820
tgccactccc actgtccttt cctaataaaa tgaggaaatt gcatcgcatt gtctgagtag    2880
gtgtcattct attctgggg gtggggtggg gcaggacagc aagggggagg attgggaaga    2940
caatagcagg catgctgggg atgcggtggg ctctatggct tctgaggcgg aaagaaccag    3000
ctggggctct aggggggtatc cccacgcgcc ctgtagcggc gcattaagcg cggcgggtgt    3060
ggtggttacg cgcagcgtga ccgctacact tgccagcgcc ctagcgcccg ctcctttcgc    3120
tttcttccct tccttctcg ccacgttcgc cggctttccc cgtcaagctc taaatcgggg    3180
gctcccttta gggttccgat ttagtgcttt acggcacctc gaccccaaaa aacttgatta    3240
gggtgatggt tcacgtagtg gccatcgcc ctgatagacg gttttcgcc ctttgacgtt    3300
ggagtccacg ttctttaata gtggactctt gttccaaact ggaacaacac tcaaccctat    3360
ctcggtctat tcttttgatt tataagggat tttgccgatt tcggcctatt ggttaaaaaa    3420
tgagctgatt taacaaaaat ttaacgcgaa ttaattctgt ggaatgtgtg tcagttaggg    3480
tgtggaaagt ccccaggctc cccagcaggc agaagtatgc aaagcatgca tctcaattag    3540
tcagcaacca ggtgtggaaa gtccccaggc tccccagcag gcagaagtat gcaaagcatg    3600
catctcaatt agtcagcaac catagtcccg cccctaactc cgcccatccc gcccctaact    3660
ccgcccagtt ccgcccattc tccgccccat ggctgactaa ttttttttat ttatgcagag    3720
```

-continued

| | |
|---|---|
| gccgaggccg cctctgcctc tgagctattc cagaagtagt gaggaggctt ttttggaggc | 3780 |
| ctaggctttt gcaaaaagct cccgggagct tgtatatcca ttttcggatc tgatcaagag | 3840 |
| acaggatgag gatcgtttcg catgattgaa caagatggat tgcacgcagg ttctccggcc | 3900 |
| gcttgggtgg agaggctatt cggctatgac tgggcacaac agacaatcgg ctgctctgat | 3960 |
| gccgccgtgt tccggctgtc agcgcagggg cgcccggttc ttttttgtcaa gaccgacctg | 4020 |
| tccggtgccc tgaatgaact gcaggacgag gcagcgcggc tatcgtggct ggccacgacg | 4080 |
| ggcgttcctt gcgcagctgt gctcgacgtt gtcactgaag cgggaaggga ctggctgcta | 4140 |
| ttgggcgaag tgccggggca ggatctcctg tcatctcacc ttgctcctgc cgagaaagta | 4200 |
| tccatcatgg ctgatgcaat gcggcggctg catacgcttg atccggctac ctgcccattc | 4260 |
| gaccaccaag cgaaacatcg catcgagcga gcacgtactc ggatggaagc cggtcttgtc | 4320 |
| gatcaggatg atctggacga agagcatcag gggctcgcgc cagccgaact gttcgccagg | 4380 |
| ctcaaggcgc gcatgcccga cggcgaggat ctcgtcgtga cccatggcga tgcctgcttg | 4440 |
| ccgaatatca tggtggaaaa tggccgcttt tctggattca tcgactgtgg ccggctgggt | 4500 |
| gtggcggacc gctatcagga catagcgttg gctacccgtg atattgctga gagcttggc | 4560 |
| ggcgaatggg ctgaccgctt cctcgtgctt tacggtatcg ccgctcccga ttcgcagcgc | 4620 |
| atcgccttct atcgccttct tgacgagttc ttctgagcgg gactctgggg ttcgaaatga | 4680 |
| ccgaccaagc gacgcccaac ctgccatcac gagatttcga ttccaccgcc gccttctatg | 4740 |
| aaaggttggg cttcggaatc gttttccggg acgccggctg gatgatcctc cagcgcgggg | 4800 |
| atctcatgct ggagttcttc gcccacccca acttgtttat tgcagcttat aatggttaca | 4860 |
| aataaagcaa tagcatcaca aatttcacaa ataaagcatt ttttttcactg cattctagtt | 4920 |
| gtggtttgtc caaactcatc aatgtatctt atcatgtctg tataccgtcg acctctagct | 4980 |
| agagcttggc gtaatcatgg tcatagctgt ttcctgtgtg aaattgttat ccgctcacaa | 5040 |
| ttccacacaa catacgagcc ggaagcataa agtgtaaagc ctggggtgcc taatgagtga | 5100 |
| gctaactcac attaattgcg ttgcgctcac tgcccgcttt ccagtcggga aacctgtcgt | 5160 |
| gccagctgca ttaatgaatc ggccaacgcg cggggagagg cggtttgcgt attgggcgct | 5220 |
| cttccgcttc ctcgctcact gactcgctgc gctcggtcgt tcggctgcgg cgagcggtat | 5280 |
| cagctcactc aaaggcggta atacggttat ccacagaatc aggggataac gcaggaaaga | 5340 |
| acatgtgagc aaaaggccag caaaaggcca ggaaccgtaa aaaggccgcg ttgctggcgt | 5400 |
| ttttccatag gctccgcccc cctgacgagc atcacaaaaa tcgacgctca agtcagaggt | 5460 |
| ggcgaaaccc gacaggacta taaagatacc aggcgtttcc ccctggaagc tccctcgtgc | 5520 |
| gctctcctgt tccgaccctg ccgcttaccg gatacctgtc cgcctttctc ccttcgggaa | 5580 |
| gcgtggcgct ttctcatagc tcacgctgta ggtatctcag ttcggtgtag gtcgttcgct | 5640 |
| ccaagctggg ctgtgtgcac gaaccccccg ttcagcccga ccgctgcgcc ttatccggta | 5700 |
| actatcgtct tgagtccaac ccggtaagac acgacttatc gccactggca gcagccactg | 5760 |
| gtaacaggat tagcagagcg aggtatgtag gcggtgctac agagttcttg aagtggtggc | 5820 |
| ctaactacgg ctacactaga agaacagtat ttggtatctg cgctctgctg aagccagtta | 5880 |
| ccttcggaaa aagagttggt agctcttgat ccggcaaaca aaccaccgct ggtagcggtt | 5940 |
| ttttttgtttg caagcagcag attacgcgca gaaaaaaagg atctcaagaa gatcctttga | 6000 |
| tcttttctac ggggtctgac gctcagtgga acgaaaactc acgttaaggg attttggtca | 6060 |

```
tgagattatc aaaaaggatc ttcacctaga tccttttaaa ttaaaaatga agtttttaaat    6120 caatctaaag tatatatgag taaacttggt ctgacagtta ccaatgctta atcagtgagg    6180
cacctatctc agcgatctgt ctatttcgtt catccatagt tgcctgactc cccgtcgtgt    6240
agataactac gatacgggag ggcttaccat ctggccccag tgctgcaatg ataccgcgag    6300
acccacgctc accggctcca gatttatcag caataaacca gccagccgga agggccgagc    6360
gcagaagtgg tcctgcaact ttatccgcct ccatccagtc tattaattgt tgccgggaag    6420
ctagagtaag tagttcgcca gttaatagtt tgcgcaacgt tgttgccatt gctacaggca    6480
tcgtggtgtc acgctcgtcg tttggtatgg cttcattcag ctccggttcc caacgatcaa    6540
ggcgagttac atgatccccc atgttgtgca aaaaagcggt tagctccttc ggtcctccga    6600
tcgttgtcag aagtaagttg gccgcagtgt tatcactcat ggttatggca gcactgcata    6660
attctcttac tgtcatgcca tccgtaagat gcttttctgt gactggtgag tactcaacca    6720
agtcattctg agaatagtgt atgcggcgac cgagttgctc ttgcccggcg tcaatacggg    6780
ataataccgc gccacatagc agaactttaa aagtgctcat cattggaaaa cgttcttcgg    6840
ggcgaaaact ctcaaggatc ttaccgctgt tgagatccag ttcgatgtaa ccccactcgtg    6900 cacccaactg atcttcagca tcttttactt tcaccagcgt ttctgggtga gcaaaaacag    6960
gaaggcaaaa tgccgcaaaa aagggaataa gggcgacacg gaaatgttga atactcatac    7020
tcttcctttt tcaatattat tgaagcattt atcagggtta ttgtctcatg agcggataca    7080
tatttgaatg tatttagaaa aataaacaaa taggggttcc gcgcacattt ccccgaaaag    7140
tgccacctga cgtc                                                       7154

<210> SEQ ID NO 5
<211> LENGTH: 7151
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (232)..(819)
<223> OTHER INFORMATION: CMV promoter
<220> FEATURE:
<221> NAME/KEY: misc_feature
<222> LOCATION: (923)..(986)
<223> OTHER INFORMATION: T8 sequence leader
<220> FEATURE:
<221> NAME/KEY: misc_feature
<222> LOCATION: (1004)..(1027)
<223> OTHER INFORMATION: flag tag
<220> FEATURE:
<221> NAME/KEY: misc_feature
<222> LOCATION: (1046)..(1591)
<223> OTHER INFORMATION: snap tag
<220> FEATURE:
<221> NAME/KEY: misc_feature
<222> LOCATION: (1598)..(2713)
<223> OTHER INFORMATION: gene of interest
<220> FEATURE:
<221> NAME/KEY: misc_feature
<222> LOCATION: (2751)..(2975)
<223> OTHER INFORMATION: BGH polyA
<220> FEATURE:
<221> NAME/KEY: misc_feature
<222> LOCATION: (3859)..(4653)
<223> OTHER INFORMATION: Neo R
<220> FEATURE:
<221> NAME/KEY: misc_feature
<222> LOCATION: (6155)..(7015)
<223> OTHER INFORMATION: Ampi R
```

```
<400> SEQUENCE: 5
gacggatcgg gagatctccc gatccctat  ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagctttgag acatggcctt accagtgacc gccttgctcc tgccgctggc     960
cttgctgctc cacgccgcca ggccggccgc cgctagcggc atcgactaca aggacgacga    1020
tgacaaggcc ggcatcgatg ccatcatgga caaagactgc gaaatgaagc gcaccaccct    1080
ggatagccct ctgggcaagc tggaactgtc tgggtgcgaa cagggcctgc acagagatcaa   1140 gctgctgggc aaaggaacat ctgccgccga cgccgtggaa gtgcctgccc cagccgccgt    1200
gctgggcgga ccagagccac tgatgcaggc caccgcctgg ctcaacgcct actttcacca    1260
gcctgaggcc atcgaggagt ccctgtgcc  agccctgcac cacccagtgt tccagcagga    1320
gagctttacc cgccaggtgc tgtggaaact gctgaaagtg gtgaagttcg agaggtcat     1380 cagctaccag cagctggccg ccctggccgg caatcccgcc gccaccgccg ccgtgaaaac    1440
cgccctgagc ggaaatcccg tgcccattct gatcccctgc caccgggtgg tgtctagctc    1500
tggcgccgtg gggggctacg agggcgggct cgccgtgaaa gagtggctgc tggcccacga    1560
gggccacaga ctgggcaagc tgggctgggt gatatcgaa  ccggccccct ccgccggcgc    1620
cgagctgcag cccccgctct tcgccaacgc ctcggacgcc tacctagcg  cctgccccag    1680 cgctggcgcc aatgcgtcgg ggccgccagg cgcgcggagc gcctcgtccc tcgccctggc    1740
aatcgccatc accgcgctct actcggccgt gtgcgccgtg gggctgctgg gcaacgtgct    1800
tgtcatgttc ggcatcgtcc ggtacactaa gatgaagacg gccaccaaca tctacatctt    1860
caacctggcc ttagccgatg cgctggccac cagcacgctg cctttccaga gtgccaagta    1920
cctgatggag acgtggccct tcggcgagct gctctgcaag gctgtgctct ccatcgacta    1980
ctacaatatg ttcaccagca tcttcacgct caccatgatg agtgttgacc gctacatcgc    2040
tgtctgccac cctgtcaagg ccctggactt ccgcacgcct gccaaggcca agctgatcaa    2100
catctgtatc tgggtcctgg cctcaggcgt tggcgtgccc atcatggtca tggctgtgac    2160
ccgtccccgg gacggggcag tggtgtgcat gctccagttc cccagcccca gctggtactg    2220
ggacacggtg accaagatct gcgtgttcct cttcgccttc gtggtgccca tcctcatcat    2280
caccgtgtgc tatggcctca tgctgctgcg cctgcgcagt gtgcgcctgc tgtcgggctc    2340
```

-continued

```
caaggagaag gaccgcagcc tgcggcgcat cacgcgcatg gtgctggtgg ttgtgggcgc    2400
cttcgtggtg tgttgggcgc ccatccacat cttcgtcatc gtctggacgc tggtggacat    2460
cgaccggcgc gacccgctgg tggtggctgc gctgcacctg tgcatcgcgc tgggctacgc    2520
caatagcagc ctcaaccccg tgctctacgc tttcctcgac gagaacttca agcgctgctt    2580
ccgccagctc tgccgcaagc cctgcggccg cccagacccc agcagcttca gccgcgcccg    2640
cgaagccacg gcccgcgagc gtgtcaccgc ctgcaccccg tccgatggtc ccggcggtgg    2700
cgctgccgcc tgatctagag ggcccgttta aacccgctga tcagcctcga ctgtgccttc    2760
tagttgccag ccatctgttg tttgcccctc cccgtgcct tccttgaccc tggaaggtgc      2820
cactcccact gtcctttcct aataaaatga ggaaattgca tcgcattgtc tgagtaggtg    2880
tcattctatt ctggggggtg gggtggggca ggacagcaag ggggaggatt gggaagacaa    2940
tagcaggcat gctggggatg cggtgggctc tatggcttct gaggcggaaa gaaccagctg    3000
gggctctagg gggtatcccc acgcgccctg tagcggcgca ttaagcgcgg cgggtgtggt    3060
ggttacgcgc agcgtgaccg ctacacttgc cagcgcccta gcgcccgctc ctttcgcttt    3120
cttcccttcc tttctcgcca cgttcgccgg ctttccccgt caagctctaa atcgggggct    3180
ccctttaggg ttccgattta gtgctttacg gcacctcgac cccaaaaaac ttgattaggg    3240
tgatggttca cgtagtgggc catcgccctg atagacggtt tttcgccctt tgacgttgga    3300
gtccacgttc tttaatagtg gactcttgtt ccaaactgga acaacactca accctatctc    3360
ggtctattct tttgatttat aagggatttt gccgatttcg gcctattggt taaaaaatga    3420
gctgatttaa caaaaattta acgcgaatta attctgtgga atgtgtgtca gttagggtgt    3480
ggaaagtccc caggctcccc agcaggcaga agtatgcaaa gcatgcatct caattagtca    3540
gcaaccaggt gtggaaagtc cccaggctcc ccagcaggca gaagtatgca aagcatgcat    3600
ctcaattagt cagcaaccat agtcccgccc ctaactccgc ccatcccgcc ctaactccg     3660 cccagttccg cccattctcc gccccatggc tgactaattt ttttatttta tgcagaggcc    3720
gaggccgcct ctgcctctga gctattccag aagtagtgag gaggcttttt tggaggccta    3780
ggcttttgca aaaagctccc gggagcttgt atatccattt tcggatctga tcaagagaca    3840
ggatgaggat cgtttcgcat gattgaacaa gatggattgc acgcaggttc tccggccgct    3900
tgggtggaga ggctattcgg ctatgactgg gcacaacaga caatcggctg ctctgatgcc    3960
gccgtgttcc ggctgtcagc gcaggggcgc ccggttcttt ttgtcaagac cgacctgtcc    4020
ggtgccctga tgaactgcag gacgaggca gcgcggctat cgtggctggc cacgacgggc     4080
gttccttgcg cagctgtgct cgacgttgtc actgaagcgg gaagggactg gctgctattg    4140
ggcgaagtgc cggggcagga tctcctgtca tctcaccttg ctcctgccga aaagtatcc     4200 atcatggctg atgcaatgcg gcggctgcat acgcttgatc cggctacctg cccattcgac    4260
caccaagcga aacatcgcat cgagcgagca cgtactcgga tggaagccgg tcttgtcgat    4320
caggatgatc tggacgaaga gcatcagggg ctcgcgccag ccgaactgtt cgccaggctc    4380
aaggcgcgca tgcccgacgg cgaggatctc gtcgtgaccc atggcgatgc ctgcttgccg    4440
aatatcatgg tggaaaatgg ccgcttttct ggattcatcg actgtggccg gctgggtgtg    4500
gcggaccgct atcaggacat agcgttggct acccgtgata ttgctgaaga gcttggcggc    4560
gaatgggctg accgcttcct cgtgctttac ggtatcgccg ctcccgattc gcagcgcatc    4620
gccttctatc gccttcttga cgagttcttc tgagcgggac tctggggttc gaaatgaccg    4680
accaagcgac gcccaacctg ccatcacgag atttcgattc caccgccgcc ttctatgaaa    4740
```

| | |
|---|---|
| ggttgggctt cggaatcgtt ttccgggacg ccggctggat gatcctccag cgcggggatc | 4800 |
| tcatgctgga gttcttcgcc cacccccaact tgtttattgc agcttataat ggttacaaat | 4860 |
| aaagcaatag catcacaaat ttcacaaata aagcattttt ttcactgcat tctagttgtg | 4920 |
| gtttgtccaa actcatcaat gtatcttatc atgtctgtat accgtcgacc tctagctaga | 4980 |
| gcttggcgta atcatggtca tagctgtttc ctgtgtgaaa ttgttatccg ctcacaattc | 5040 |
| cacacaacat acgagccgga agcataaagt gtaaagcctg gggtgcctaa tgagtgagct | 5100 |
| aactcacatt aattgcgttg cgctcactgc ccgctttcca gtcgggaaac ctgtcgtgcc | 5160 |
| agctgcatta atgaatcggc caacgcgcgg ggagaggcgg tttgcgtatt gggcgctctt | 5220 |
| ccgcttcctc gctcactgac tcgctgcgct cggtcgttcg gctgcggcga gcggtatcag | 5280 |
| ctcactcaaa ggcggtaata cggttatcca cagaatcagg ggataacgca ggaaagaaca | 5340 |
| tgtgagcaaa aggccagcaa aaggccagga accgtaaaaa ggccgcgttg ctggcgtttt | 5400 |
| tccataggct ccgcccccct gacgagcatc acaaaaatcg acgctcaagt cagaggtggc | 5460 |
| gaaacccgac aggactataa agataccagg cgtttccccc tggaagctcc ctcgtgcgct | 5520 |
| ctcctgttcc gaccctgccg cttaccggat acctgtccgc ctttctccct tcgggaagcg | 5580 |
| tggcgctttc tcatagctca cgctgtaggt atctcagttc ggtgtaggtc gttcgctcca | 5640 |
| agctgggctg tgtgcacgaa ccccccgttc agcccgaccg ctgcgcctta tccggtaact | 5700 |
| atcgtcttga gtccaacccg gtaagacacg acttatcgcc actggcagca gccactggta | 5760 |
| acaggattag cagagcgagg tatgtaggcg gtgctacaga gttcttgaag tggtggccta | 5820 |
| actacggcta cactagaaga acagtatttg gtatctgcgc tctgctgaag ccagttacct | 5880 |
| tcggaaaaag agttggtagc tcttgatccg gcaaacaaac caccgctggt agcggttttt | 5940 |
| ttgtttgcaa gcagcagatt acgcgcagaa aaaaggatc tcaagaagat cctttgatct | 6000 |
| tttctacggg gtctgacgct cagtggaacg aaaactcacg ttaagggatt ttggtcatga | 6060 |
| gattatcaaa aaggatcttc acctagatcc ttttaaatta aaaatgaagt tttaaatcaa | 6120 |
| tctaaagtat atatgagtaa acttggtctg acagttacca atgcttaatc agtgaggcac | 6180 |
| ctatctcagc gatctgtcta tttcgttcat ccatagttgc ctgactcccc gtcgtgtaga | 6240 |
| taactacgat acgggagggc ttaccatctg gccccagtgc tgcaatgata ccgcgagacc | 6300 |
| cacgctcacc ggctccagat ttatcagcaa taaaccagcc agccggaagg gccgagcgca | 6360 |
| gaagtggtcc tgcaacttta tccgcctcca tccagtctat taattgttgc cgggaagcta | 6420 |
| gagtaagtag ttcgccagtt aatagtttgc gcaacgttgt tgccattgct acaggcatcg | 6480 |
| tggtgtcacg ctcgtcgttt ggtatggctt cattcagctc cggttcccaa cgatcaaggc | 6540 |
| gagttacatg atcccccatg ttgtgcaaaa aagcggttag ctccttcggt cctccgatcg | 6600 |
| ttgtcagaag taagttggcc gcagtgttat cactcatggt tatggcagca ctgcataatt | 6660 |
| ctcttactgt catgccatcc gtaagatgct tttctgtgac tggtgagtac tcaaccaagt | 6720 |
| cattctgaga atagtgtatg cggcgaccga gttgctcttg cccggcgtca atacgggata | 6780 |
| ataccgcgcc acatagcaga actttaaaag tgctcatcat tggaaaacgt tcttcggggc | 6840 |
| gaaaactctc aaggatctta ccgctgttga tccagttcga tgtaaccca ctcgtgcac | 6900 |
| ccaactgatc ttcagcatct tttactttca ccagcgtttc tgggtgagca aaaacaggaa | 6960 |
| ggcaaaatgc cgcaaaaaag ggaataaggg cgacacggaa atgttgaata ctcatactct | 7020 |
| tccttttcca atattattga agcatttatc agggttattg tctcatgagc ggatacatat | 7080 | ttgaatgtat ttagaaaaat aaacaaatag gggttccgcg cacatttccc cgaaaagtgc    7140 cacctgacgt c                                                         7151

<210> SEQ ID NO 6
<211> LENGTH: 7619
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (232)..(819)
<223> OTHER INFORMATION: CMV promoter
<220> FEATURE:
<221> NAME/KEY: misc_feature
<222> LOCATION: (923)..(986)
<223> OTHER INFORMATION: T8 leader sequence
<220> FEATURE:
<221> NAME/KEY: misc_feature
<222> LOCATION: (1004)..(1027)
<223> OTHER INFORMATION: flag tag
<220> FEATURE:
<221> NAME/KEY: misc_feature
<222> LOCATION: (1040)..(1927)
<223> OTHER INFORMATION: halo tag
<220> FEATURE:
<221> NAME/KEY: misc_feature
<222> LOCATION: (1934)..(3181)
<223> OTHER INFORMATION: gene of interest
<220> FEATURE:
<221> NAME/KEY: misc_feature
<222> LOCATION: (3219)..(3443)
<223> OTHER INFORMATION: BGH polyA
<220> FEATURE:
<221> NAME/KEY: misc_feature
<222> LOCATION: (4327)..(5121)
<223> OTHER INFORMATION: Neo R
<220> FEATURE:
<221> NAME/KEY: misc_feature
<222> LOCATION: (6623)..(7483)
<223> OTHER INFORMATION: Ampi R

<400> SEQUENCE: 6
gacggatcgg gagatctccc gatccctat ggtgcactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgag acatggcctt accagtgacc gccttgctcc tgccgctggc    960
cttgctgctc cacgccgcca ggccggccgc cgctagcggc atcgactaca aggacgacga    1020

```
tgacaaggcc ggcatcgatg cagaaatcgg tactggcttt ccattcgacc cccattatgt    1080
ggaagtcctg ggcgagcgca tgcactacgt cgatgttggt ccgcgcgatg gcacccctgt    1140
gctgttcctg cacggtaacc cgacctcctc ctacgtgtgg cgcaacatca tcccgcatgt    1200
tgcaccgacc catcgctgca ttgctccaga cctgatcggt atgggcaaat ccgacaaacc    1260
agacctgggt tatttcttcg acgaccacgt ccgcttcatg gatgccttca tcgaagccct    1320
gggtctggaa gaggtcgtcc tggtcattca cgactgggc tccgctctgg gtttccactg    1380
ggccaagcgc aatccagagc gcgtcaaagg tattgcattt atggagttca tccgccctat    1440
cccgacctgg gacgaatggc cagaatttgc ccgcgagacc ttccaggcct tccgcaccac    1500
cgacgtcggc cgcaagctga tcatcgatca gaacgttttt atcgagggta cgctgccgat    1560
gggtgtcgtc cgcccgctga ctgaagtcga gatggaccat taccgcgagc cgttcctgaa    1620
tcctgttgac cgcgagccac tgtggcgctt cccaaacgag ctgccaatcg ccggtgagcc    1680
agcgaacatc gtcgcgctgg tcgaagaata catggactgg ctgcaccagt cccctgtccc    1740
gaagctgctg ttctggggca ccccaggcgt tctgatccca ccggccgaag ccgctcgcct    1800
ggccaaaagc ctgcctaact gcaaggctgt ggacatcggc ccgggtctga atctgctgca    1860
agaagacaac ccggacctga tcggcagcga gatcgcgcgc tggctgtcga cgctcgagat    1920
ttccggcgat atcgatccac tgaatctgtc ctggtatgat gatgatctgg agaggcagaa    1980
ctggagccgg cccttcaacg ggtcagacgg gaaggcggac agacccccact acaactacta    2040 tgccacactg ctcaccctgc tcatcgctgt catcgtcttc ggcaacgtgc tggtgtgcat    2100
ggctgtgtcc cgcgagaagg cgctgcagac caccaccaac tacctgatcg tcagcctcgc    2160
agtggccgac ctcctcgtcg ccacactggt catgcccctgg gttgtctacc tggaggtggt    2220
aggtgagtgg aaattcagca ggattcactg tgacatcttc gtcactctgg acgtcatgat    2280
gtgcacggcg agcatcctga acttgtgtgc catcagcatc gacaggtaca cagctgtggc    2340
catgcccatg ctgtacaata cgcgctacag ctccaagcgc cgggtcaccg tcatgatctc    2400
catcgtctgg gtcctgtcct tcaccatctc ctgcccactc ctcttcggac tcaataacgc    2460
agaccagaac gagtgcatca ttgccaaccc ggccttcgtg gtctactcct ccatcgtctc    2520
cttctacgtg cccttcattg tcaccctgct ggtctacatc aagatctaca ttgtcctccg    2580
cagacgccga aagcgagtca acaccaaacg cagcagccga gctttcaggg cccacctgag    2640
ggctccacta aaggaggctg cccggcgagc ccaggagctg gagatggaga tgctctccag    2700
caccagccca cccgagagga cccggtacag ccccatccca cccagccacc accagctgac    2760
tctccccgac ccgtcccacc atggtctcca cagcactccc gacagccccg ccaaaccaga    2820
gaagaatggg catgccaaag accacccaa gattgccaag atctttgaga tccagaccat    2880
gcccaatggc aaaacgcgta cctccctcaa gaccatgagc cgtaggaagc tctcccagca    2940
gaaggagaag aaagccactc agatgctcgc cattgttctc ggcgtgttca tcatctgctg    3000
gctgcccttc ttcatcacac acatcctgaa catacactgt gactgcaaca tcccgcctgt    3060
cctgtacagc gccttcacgt ggctgggcta tgtcaacagc gccgtgaacc ccatcatcta    3120
caccaccttc aacattgagt ccgcaaggc cttcctgaag atcctccact gctgactcga    3180
gtctagaggg cccgtttaaa cccgctgatc agcctcgact gtgccttcta gttgccagcc    3240
atctgttgtt tgcccctccc ccgtgccttc cttgaccctg gaaggtgcca ctcccactgt    3300
cctttcctaa taaaatgagg aaattgcatc gcattgtctg agtaggtgtc attctattct    3360
ggggggtggg gtggggcagg acagcaaggg ggaggattgg gaagacaata gcaggcatgc    3420
```

-continued

```
tggggatgcg gtgggctcta tggcttctga ggcggaaaga accagctggg gctctagggg    3480
gtatccccac gcgccctgta gcggcgcatt aagcgcggcg ggtgtggtgg ttacgcgcag    3540
cgtgaccgct acacttgcca gcgccctagc gcccgctcct ttcgctttct tcccttcctt    3600
tctcgccacg ttcgccggct ttccccgtca agctctaaat cggggctcc  ctttagggtt    3660 ccgatttagt gctttacggc acctcgaccc caaaaaactt gattagggtg atggttcacg    3720
tagtgggcca tcgccctgat agacggtttt tcgccctttg acgttggagt ccacgttctt    3780
taatagtgga ctcttgttcc aaactggaac aacactcaac cctatctcgg tctattcttt    3840
tgatttataa gggattttgc cgatttcggc ctattggtta aaaaatgagc tgatttaaca    3900
aaaatttaac gcgaattaat ctgtggaat  gtgtgtcagt tagggtgtgg aaagtcccca    3960
ggctccccag caggcagaag tatgcaaagc atgcatctca attagtcagc aaccaggtgt    4020
ggaaagtccc caggctcccc agcaggcaga agtatgcaaa gcatgcatct caattagtca    4080
gcaaccatag tcccgcccct aactccgccc atcccgcccc taactccgcc cagttccgcc    4140
cattctccgc cccatggctg actaattttt tttatttatg cagaggccga ggccgcctct    4200
gcctctgagc tattccagaa gtagtgagga ggcttttttg gaggcctagg cttttgcaaa    4260
aagctcccgg gagcttgtat atccattttc ggatctgatc aagagacagg atgaggatcg    4320
tttcgcatga ttgaacaaga tggattgcac gcaggttctc cggccgcttg ggtgagagg     4380 ctattcggct atgactgggc acaacagaca atcggctgct ctgatgccgc cgtgttccgg    4440
ctgtcagcgc aggggcgccc ggttcttttt gtcaagaccg acctgtccgg tgccctgaat    4500
gaactgcagg acgaggcagc gcggctatcg tggctggcca cgacgggcgt tccttgcgca    4560
gctgtgctcg acgttgtcac tgaagcggga agggactggc tgctattggg cgaagtgccg    4620
gggcaggatc tcctgtcatc tcaccttgct cctgccgaga aagtatccat catggctgat    4680
gcaatgcggc ggctgcatac gcttgatccg gctacctgcc cattcgacca ccaagcgaaa    4740
catcgcatcg agcgagcacg tactcggatg aagccggtc  ttgtcgatca ggatgatctg    4800
gacgaagagc atcaggggct cgcgccagcc gaactgttcg ccaggctcaa ggcgcgcatg    4860
cccgacggcg aggatctcgt cgtgacccat ggcgatgcct gcttgccgaa tatcatggtg    4920
gaaaatggcc gcttttctgg attcatcgac tgtggccggc tgggtgtggc ggaccgctat    4980
caggacatag cgttggctac ccgtgatatt gctgaagagc ttggcggcga atgggctgac    5040
cgcttcctcg tgctttacgg tatcgccgct cccgattcgc agcgcatcgc cttctatcgc    5100
cttcttgacg agttcttctg agcgggactc tggggttcga aatgaccgac caagcgacgc    5160
ccaacctgcc atcacgagat ttcgattcca ccgccgcctt ctatgaaagg ttgggcttcg    5220
gaatcgtttt ccgggacgcc ggctggatga tcctccagcg cggggatctc atgctggagt    5280
tcttcgccca ccccaacttg tttattgcag cttataatgg ttacaaataa agcaatagca    5340
tcacaaattt cacaaataaa gcattttttt cactgcattc tagttgtggt ttgtccaaac    5400
tcatcaatgt atcttatcat gtctgtatac cgtcgacctc tagctagagc ttggcgtaat    5460
catggtcata gctgtttcct gtgtgaaatt gttatccgct cacaattcca cacaacatac    5520
gagccggaag cataaagtgt aaagcctggg gtgcctaatg agtgagctaa ctcacattaa    5580
ttgcgttgcg ctcactgccc gctttccagt cgggaaacct gtcgtgccag ctgcattaat    5640
gaatcggcca acgcgcgggg agaggcggtt tgcgtattgg gcgctcttcc gcttcctcgc    5700
tcactgactc gctgcgctcg gtcgttcggc tgcggcgagc ggtatcagct cactcaaagg    5760
cggtaatacg gttatccaca gaatcagggg ataacgcagg aaagaacatg tgagcaaaag    5820
```

```
gccagcaaaa ggccaggaac cgtaaaaagg ccgcgttgct ggcgttttc cataggctcc    5880
gcccccctga cgagcatcac aaaaatcgac gctcaagtca gaggtggcga aacccgacag    5940
gactataaag ataccaggcg tttcccctg gaagctccct cgtgcgctct cctgttccga    6000
ccctgccgct taccggatac ctgtccgcct ttctcccttc gggaagcgtg gcgctttctc    6060
atagctcacg ctgtaggtat ctcagttcgg tgtaggtcgt tcgctccaag ctgggctgtg    6120
tgcacgaacc ccccgttcag cccgaccgct gcgccttatc cggtaactat cgtcttgagt    6180
ccaacccggt aagacacgac ttatcgccac tggcagcagc cactggtaac aggattagca    6240
gagcgaggta tgtaggcggt gctacagagt tcttgaagtg gtggcctaac tacggctaca    6300
ctagaagaac agtatttggt atctgcgctc tgctgaagcc agttaccttc ggaaaaagag    6360
ttggtagctc ttgatccggc aaacaaacca ccgctggtag cggttttttt gtttgcaagc    6420
agcagattac gcgcagaaaa aaaggatctc aagaagatcc tttgatcttt tctacggggt    6480
ctgacgctca gtggaacgaa aactcacgtt aagggatttt ggtcatgaga ttatcaaaaa    6540
ggatcttcac ctagatcctt ttaaattaaa aatgaagttt taaatcaatc taaagtatat    6600
atgagtaaac ttggtctgac agttaccaat gcttaatcag tgaggcacct atctcagcga    6660
tctgtctatt tcgttcatcc atagttgcct gactccccgt cgtgtagata actacgatac    6720
gggagggctt accatctggc cccagtgctg caatgatacc gcgagaccca cgctcaccgg    6780
ctccagattt atcagcaata aaccagccag ccggaagggc cgagcgcaga agtggtcctg    6840
caactttatc cgcctccatc cagtctatta attgttgccg ggaagctaga gtaagtagtt    6900
cgccagttaa tagtttgcgc aacgttgttg ccattgctac aggcatcgtg gtgtcacgct    6960
cgtcgtttgg tatggcttca ttcagctccg gttcccaacg atcaaggcga gttacatgat    7020
cccccatgtt gtgcaaaaaa gcggttagct ccttcggtcc tccgatcgtt gtcagaagta    7080
agttggccgc agtgttatca ctcatggtta tggcagcact gcataattct cttactgtca    7140
tgccatccgt aagatgcttt tctgtgactg gtgagtactc aaccaagtca ttctgagaat    7200
agtgtatgcg gcgaccgagt tgctcttgcc cggcgtcaat acgggataat accgcgccac    7260
atagcagaac tttaaaagtg ctcatcattg gaaaacgttc ttcggggcga aaactctcaa    7320
ggatcttacc gctgttgaga tccagttcga tgtaacccac tcgtgcaccc aactgatctt    7380
cagcatcttt tactttcacc agcgtttctg ggtgagcaaa aacaggaagg caaaatgccg    7440
caaaaaaggg aataagggcg acacggaaat gttgaatact catactcttc ctttttcaat    7500
attattgaag catttatcag ggttattgtc tcatgagcgg atacatattt gaatgtattt    7560
agaaaaataa acaaataggg gttccgcgca catttccccg aaaagtgcca cctgacgtc    7619
```